US012741126B2

(12) United States Patent
Irving et al.

(10) Patent No.: US 12,741,126 B2
(45) Date of Patent: Sep. 22, 2026

(54) DUAL-DENSITY FORMULATIONS DEVICES AND METHODS FOR INTRANASAL DRUG DELIVERY OR SAMPLING

(71) Applicant: Rocket Science Health Corp., Victoria (CA)

(72) Inventors: Kenneth Irving, Victoria (CA); James Jackson, Victoria (CA); Alec Lillis, Victoria (CA); Timothy Rees, Victoria (CA)

(73) Assignee: Rocket Science Health Corp., Victoria (CA)

( * ) Notice: Subject to any disclaimer, the term of this patent is extended or adjusted under 35 U.S.C. 154(b) by 0 days.

(21) Appl. No.: 19/209,192

(22) Filed: May 15, 2025

(65) Prior Publication Data

US 2025/0269159 A1 Aug. 28, 2025

Related U.S. Application Data

(63) Continuation of application No. PCT/IB2024/059369, filed on Sep. 25, 2024.

(Continued)

(51) Int. Cl.

*A61M 31/00* (2006.01)
*A61B 10/00* (2006.01)
*A61M 3/00* (2006.01)

(52) U.S. Cl.

CPC ......... *A61M 31/00* (2013.01); *A61B 10/0045* (2013.01); *A61M 3/005* (2013.01);

(Continued)

(58) Field of Classification Search

None

See application file for complete search history.

(56) References Cited

U.S. PATENT DOCUMENTS

2001/0004644 A1* 6/2001 Levin .................... A61M 15/08 514/646
2012/0323214 A1* 12/2012 Shantha ............... A61N 1/0546 604/501

(Continued)

FOREIGN PATENT DOCUMENTS

WO 2020217097 A1 10/2020
WO 2021066195 A1 4/2021

(Continued)

OTHER PUBLICATIONS

International Search Report and Written Opinion received in PCT Application No. PCT/IB2024/059369, mailed on Jan. 29, 2025, 7 pages.

(Continued)

*Primary Examiner* — Matthew Kremer

(74) *Attorney, Agent, or Firm* — Mintz, Levin, Cohn, Ferris, Glovsky and Popeo, P.C.

(57) ABSTRACT

The present disclosure describes formulations, methods, and devices for intranasal delivery to a subject. The formulations may form two fluids which are immiscible at intranasal environmental conditions, such that when a formulation is delivered to a nasal cavity the two fluids separate with the more dense of the fluids settling below the less dense of the two fluids. One or more of the two fluids may concentrate a therapeutic agent or sampling fluid against a selected portion of the nasal cavity and the more dense of the two fluids can increase retention time of the formulation within the nasal cavity. Devices of the present disclosure may provide a convenient and effective way to deliver dual-density formulations intranasally.

18 Claims, 15 Drawing Sheets

Related U.S. Application Data

(60) Provisional application No. 63/540,645, filed on Sep. 26, 2023.

(52) U.S. Cl.
CPC .................. *A61B 2217/007* (2013.01); *A61M 2210/0618* (2013.01)

(56) References Cited

U.S. PATENT DOCUMENTS

| | | | | |
|---|---|---|---|---|
| 2013/0073015 | A1* | 3/2013 | Rozenberg ........ | A61M 25/0068 607/105 |
| 2014/0242064 | A1* | 8/2014 | Morriss ................ | A61K 9/0043 424/94.67 |
| 2015/0230700 | A1* | 8/2015 | Chandler ............. | A61M 31/00 600/116 |
| 2022/0088327 | A1 | 3/2022 | Fuller et al. | |

FOREIGN PATENT DOCUMENTS

| | | | | |
|---|---|---|---|---|
| WO | WO-2021069972 | A1 * | 4/2021 | ............. G16H 20/10 |
| WO | 2022219406 | A1 | 10/2022 | |
| WO | 2025068920 | A1 | 4/2025 | |

OTHER PUBLICATIONS

Kolanjiyil et al. (2022) “Importance of Spray-Wall Interaction and Post-Deposition Liquid Motion in the Transport and Delivery of Pharmaceutical Nasal Sprays”, Pharmaceutics, 14(5):956 (26 pages).

* cited by examiner

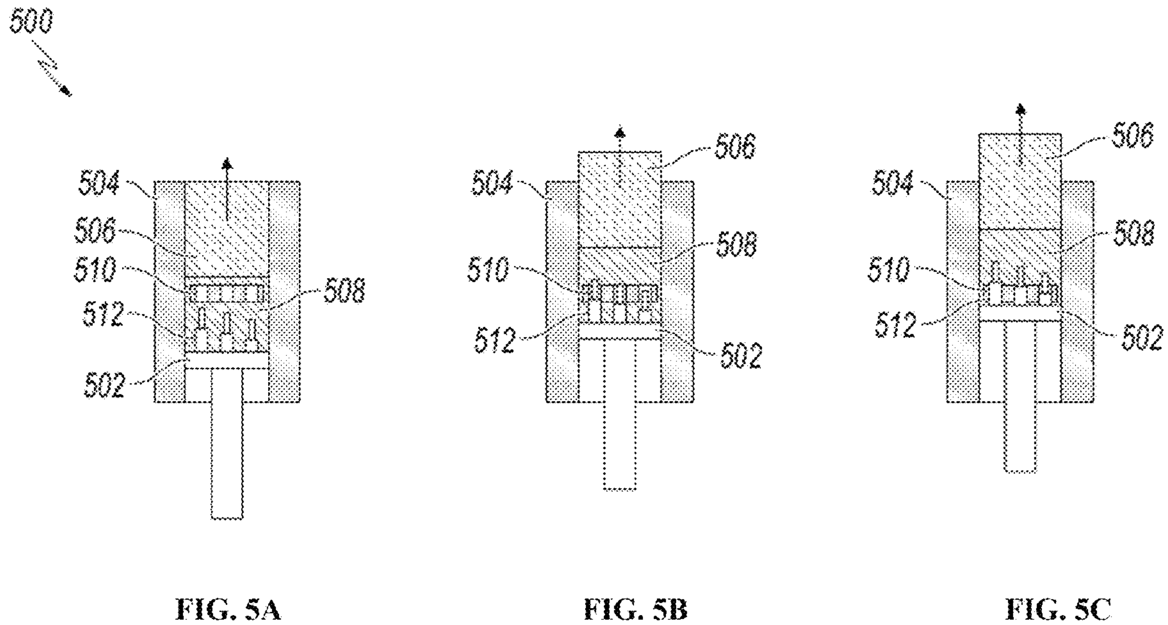
FIG. 5A
FIG. 5B
FIG. 5C
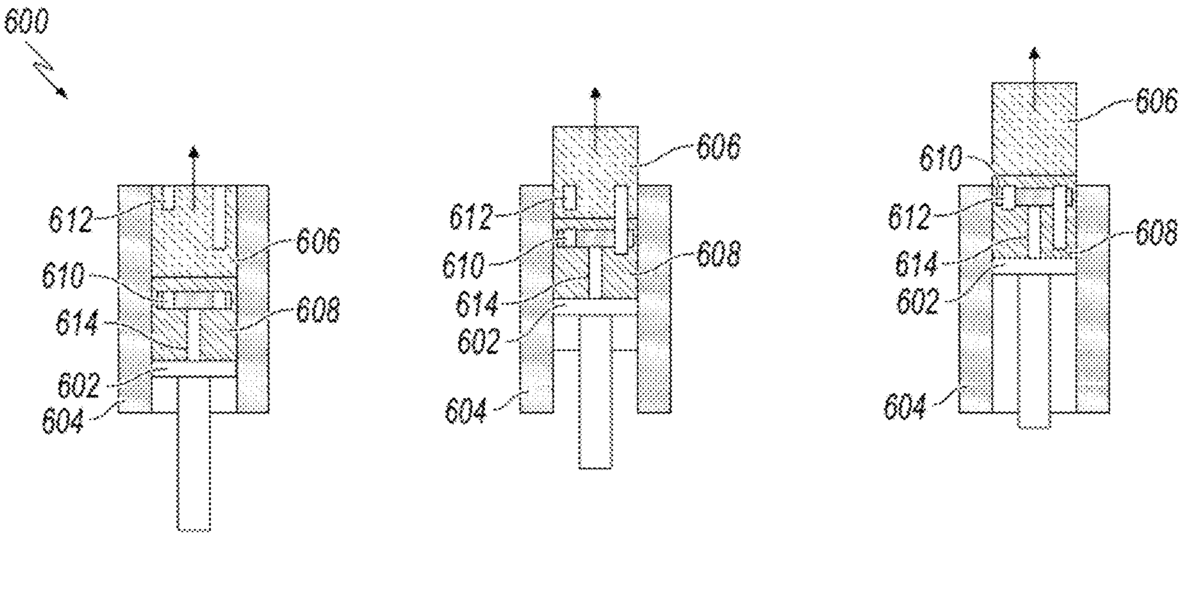
FIG. 6A
FIG. 6B
FIG. 6C

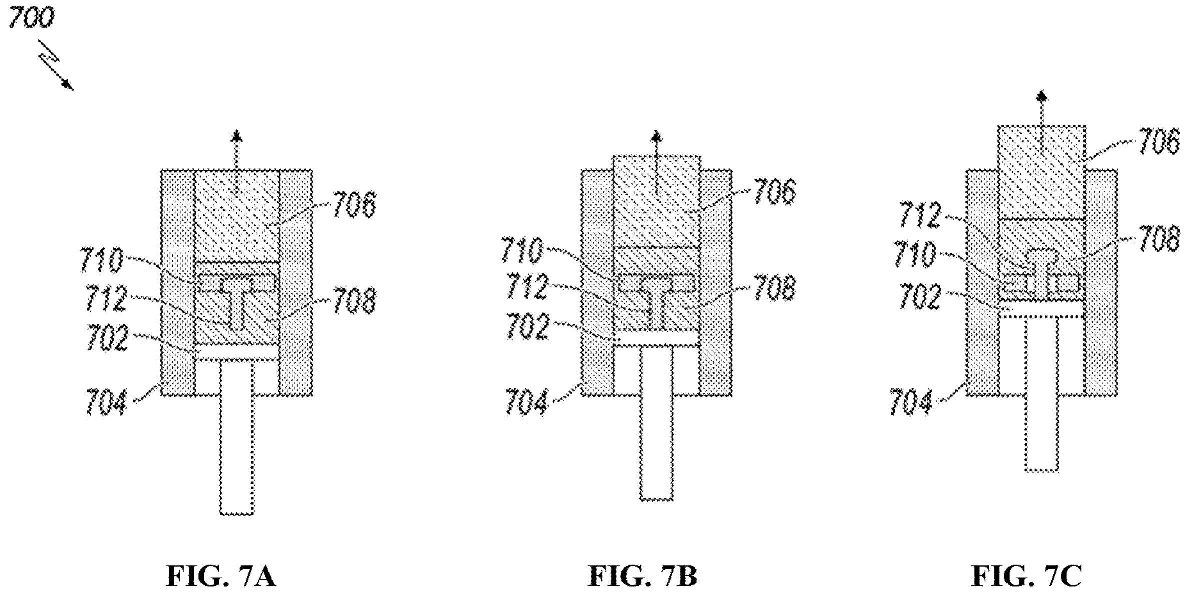
FIG. 7A
FIG. 7B
FIG. 7C
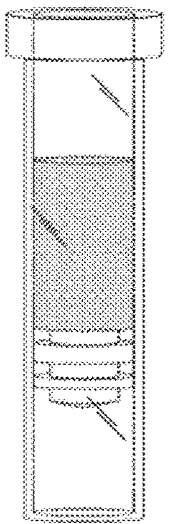
FIG. 8

DUAL-DENSITY FORMULATIONS DEVICES AND METHODS FOR INTRANASAL DRUG DELIVERY OR SAMPLING

CROSS REFERENCE

This application is a continuation of International Patent Application No. PCT/IB24/059369, filed Sep. 25, 2024, which claims the benefit to U.S. Provisional Application No. 63/540,645, filed Sep. 26, 2023, the content of each is incorporated herein by reference, including any drawings.

BACKGROUND

Intranasal drug delivery is an effective route for the administration of certain medications, for example, those that act locally in the nasal cavity, or those that are rapidly absorbed into the bloodstream through the nasal mucosa. One challenge associated with delivering compositions to the nasal channel of a subject is contacting a target area of the nasal cavity with a therapeutic agent for sufficient retention time for an effective dose to be administered to the target area. Various formulations and substances such as mucoadhesives can be used for intranasal delivery, but the selection is limited by requirements such as biocompatibility and that the therapeutic agent have sufficient solubility within the rest of the formulation. Variability of a formulation's retention time within the nasal cavity may hinder dosage precision and limit safety and efficacy. Otherwise-suitable formulations may have insufficient residence time within the nasal cavity to deliver a therapeutic dose without significant waste of therapeutic material or risk of an improper dosage level. The high cost of various therapeutic agents incentivizes efficient delivery and the minimization of residual amounts of the therapeutic agent within the delivery device. There is a need for formulations, methods, and devices for intranasal delivery with optimized retention time of therapeutic agents or sampling fluids and minimized waste.

SUMMARY

It is appreciated by the inventors that difficulties in nasal delivery include efficient delivery of therapeutic agents to target areas within the nasal cavity with sufficient retention time for administration of an effective and precision dose without excessive waste of the therapeutic agent. For example, certain hydrophobic or water-sensitive therapeutic agents may have relatively short or variable retention times within the nasal cavity.

To counter such difficulties, this disclosure provides dual-density formulations for intranasal delivery, and methods and devices for delivering the same. The formulations may form two fluids which are immiscible at intranasal environmental conditions, with the upper, or lighter, of the fluids configured to administer a therapeutic dose of a therapeutic agent to a target area of the nasal cavity of a subject, and the lower, or denser, of the two fluids configured to increase retention time of the therapeutic agent within the nasal cavity or to purge a residual amount of the therapeutic agent from the delivery device in order to maximize efficiency and repeatability of the delivery. In some embodiments, the lower fluid supports the upper fluid, for example, supporting the placement of the upper fluid in a desired region for a longer time than if the upper fluid were unsupported by the lower fluid. In some embodiments, the presence of the denser fluid helps to concentrate the lighter fluid high up along an underside of the cribriform plate. In some embodiments, the denser fluid at least partially obstructs a lower aspect of the olfactory cleft beneath the lighter fluid, for example, due to high viscosity and/or strong surface tension of the denser fluid, thereby increasing the residence time of the drug-bearing fluid.

The volume of dual-density formulation delivered to the olfactory cleft may be sufficient to fill, or partially fill, the olfactory cleft, instead of merely coating the mucus membrane. A bolus of dual-density formulation may span from one side of an olfactory cleft to another side of the olfactory cleft. In some embodiments, the lower fluid bridges between sides of the olfactory cleft so as to suspend the upper fluid within the olfactory cleft.

In one aspect is a method of concentrating a fluid against an olfactory region of a nasal cavity of a subject, the method comprising: delivering a formulation to the olfactory region of the nasal cavity, the formulation configured to form: an upper fluid; and a lower fluid, immiscible with the upper fluid at intranasal environmental conditions and having a greater density than that of the upper fluid; wherein one or more volumes of the formulation delivered to the olfactory region of the nasal cavity each form an upper layer comprising the upper fluid and a lower layer comprising the lower fluid, thereby concentrating the upper fluid against the olfactory region of the nasal cavity.

In another aspect is a formulation for intranasal delivery, the formulation configured to form:

- an upper fluid; and a lower fluid, immiscible with the upper fluid at intranasal environmental conditions and having a greater density than that of the upper fluid;
- wherein at intranasal environmental conditions, one or more volumes of the formulation each form an upper layer comprising the upper fluid and a lower layer comprising the lower fluid.

In another aspect is a device for delivery of a formulation to an olfactory region of a nasal cavity, the device comprising: one or more fluid reservoirs configured to contain a formulation configured to form: an upper fluid; and a lower fluid, immiscible with the upper fluid at intranasal environmental conditions and having a greater density than that of the upper fluid; wherein at intranasal environmental conditions, one or more volumes of the formulation each form an upper layer comprising the upper fluid and a lower layer comprising the lower fluid; a dispensing tip for delivering the formulation to the olfactory region, wherein the dispensing tip is coupled with the one or more fluid reservoirs; and a dispensing mechanism for exerting pressure on the upper fluid and on the lower fluid such that the upper fluid and the lower fluid each flow through the dispensing tip, thereby dispensing the formulation to the olfactory region.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description and accompanying drawings, that set forth illustrative embodiments in which the principles of the present disclosure are utilized.

FIGS. 5A-5C depicts a device for intranasal delivery having an internal damping mechanism with a static orifice plate with holes and moving rods (FIG. 5A). Variable diameter rods are attached to the syringe plunger and the flow path decreases or increases as holes in the orifice plate are opened or closed by the rods (FIGS. 5B-5C).

FIGS. 6A-6C depict a device for intranasal delivery having an internal damping mechanism with a moving orifice plate with holes and static rods. A fixed member connects the orifice plate to the plunger (FIG. 6A) and the flow path decreases or increases as holes in the orifice plate are opened or closed by the rods (FIG. 6B-6C).

FIGS. 7A-7C depict a device for intranasal delivery having an internal damping mechanism with a static orifice plate and a moving dumbbell-shaped pin. The orifice plate has a hole for the dumbbell-shaped pin (FIG. 7A) and as the plunger advances, it moves the pin from the orifice plate, thereby increasing the flow path (FIGS. 7B-7C).

FIG. 8 is an image and an illustration of a vial with a target dose loaded on top (shaded) and an empty volume loaded into the bottom (clear) according to some embodiments.

FIG. 9A illustrates a pre-actuation stage where the stopper is not yet punctured, the one-way valve is closed, and no liquid is moving through the system. FIG. 9B illustrates delivery of the target dose, where the stopper is punctured and is pushed down the vial by the puncture, the one-way valve is still closed, and the target dose is moving through the system. FIG. 9C illustrates delivery of the secondary dose, where the stopper is punctured and is pushed down the vial by the puncture, the one-way valve is opened and is pushed down the vial by the stopper, and the secondary dose is pushed through the system following the target dose.

DETAILED DESCRIPTION

Figure 1A:
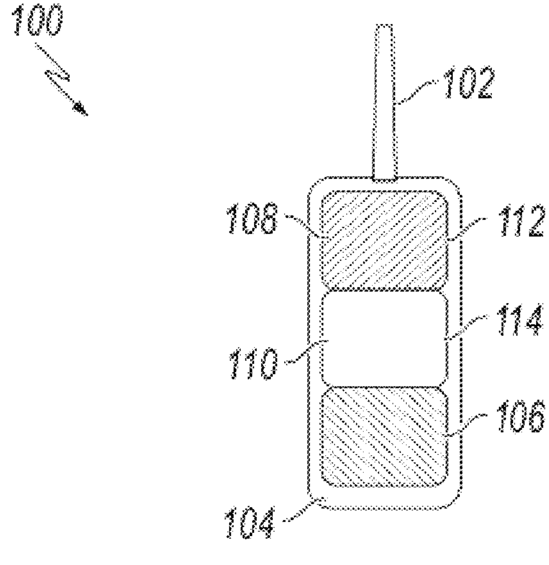
FIG. 1A depicts a device for intranasal delivery of a two-fluid formulation, wherein the fluids are stored in separate reservoirs within the device.
Figure 1B:
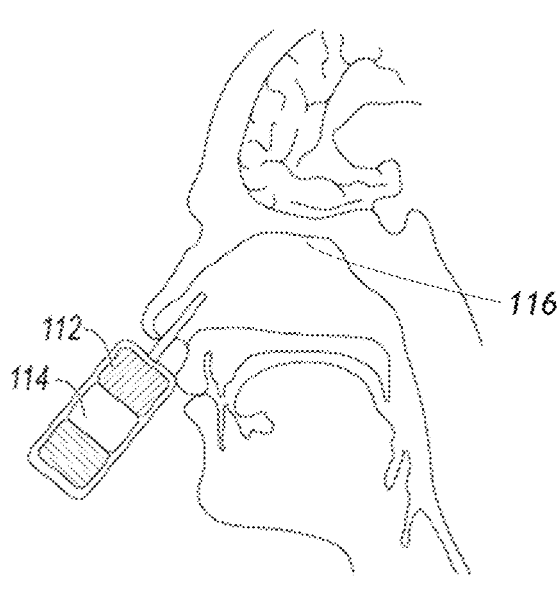
FIG. 1B is an illustration of the device inserted into a nasal cavity of the subject for olfactory delivery.
Figure 1C:
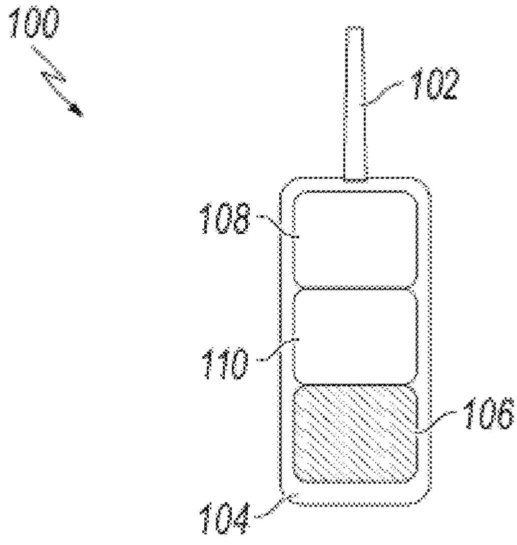
FIG. 1C depicts the device shown in FIG. 1A, after sequential delivery of the two fluids.

A variety of formulations have been proposed for intranasal delivery applications. It is appreciated by the inventors that various properties are all relevant to the design of an optimal formulation for intranasal delivery of any particular therapeutic agent or sampling fluid. For certain therapeutic agents, a single fluid may not provide adequate delivery. For example, a therapeutic agent may be insoluble or reactive in fluids having a suitable retention time in the olfactory cleft.

To counter such difficulties, this disclosure provides dual-density formulations for intranasal delivery, and methods and devices for delivering the same. In one aspect is a method of concentrating a fluid against an olfactory region of a nasal cavity of a subject, the method comprising: delivering a formulation to the olfactory region of the nasal cavity, the formulation configured to form: an upper fluid; and a lower fluid, immiscible with the upper fluid at intranasal environmental conditions; wherein one or more volumes of the formulation delivered to the olfactory region of the nasal cavity each form an upper layer comprising the upper fluid and a lower layer comprising the lower fluid, thereby concentrating the upper fluid against the olfactory region of the nasal cavity. In some embodiments, the olfactory region comprises an olfactory cleft of the nasal cavity. In some embodiments, the upper fluid comprises a therapeutic agent. In some embodiments, the therapeutic agent is preferentially soluble in the upper fluid. For example, in some embodiments, the therapeutic agent is preferentially soluble in the upper fluid such that the therapeutic agent is concentrated in the top layer, and the bottom layer is substantially free of the therapeutic agent.

In some embodiments, the upper fluid delivers the therapeutic agent to the nasal cavity, and the lower fluid increases a residence time of the therapeutic agent within the nasal cavity. In some embodiments, a residence time of the formulation in the nasal cavity is at least about 1%, at least about 2%, at least about 3%, at least about 4%, at least about 5%, at least about 6%, at least about 7%, at least about 8%, at least about 9%, at least about 10%, at least about 12%, at least about 14%, at least about 16%, at least about 18%, at least about 20%, at least about 22%, at least about 24%, at least about 26%, at least about 28%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 120%, at least about 140%, at least about 160%, at least about 180%, at least about 200%, at least about 250%, at least about 300%, at least about 350%, at least about 400%, at least about 450%, at least about 500%, at least about 600%, at least about 700%, at least about 800%, at least about 900%, at least about 1000%, at least about 1200%, at least about 1400%, at least about 1600%, at least about 1800%, at least about 2000%, at least about 2500%, at least about 3000%, at least about 3500%, at least about 4000%, at least about 4500%, at least about 5000%, at least about 6000%, at least about 7000%, at least about 8000%, at least about 9000%, at least about 10,000%, at least about 20,000%, at least about 40,000%, at least about 60,000%, at least about 80,000%, or at least about 100,000% greater than a residence time of the upper fluid alone.

In some embodiments, the upper fluid delivers the therapeutic agent to an olfactory cleft of the nasal cavity, and the lower fluid at least partially obstructs a lower aspect of an olfactory cleft of the nasal cavity. In some embodiments, the lower fluid fully obstructs a lower aspect of the olfactory cleft. In some embodiments, the lower fluid comprises a therapeutic agent. In some embodiments, the upper fluid comprises a first therapeutic agent, preferentially soluble in the upper fluid, and the lower fluid comprises a second therapeutic agent, preferentially soluble in the lower fluid. In some embodiments, the first therapeutic agent is delivered to an olfactory region of the subject, and the second therapeutic agent affects a tissue so as to influence absorption of the first therapeutic agent. For example, the second therapeutic agent may affect the tissue to increase or to decrease absorption of the first therapeutic agent. In some embodiments, the second therapeutic agent promotes or prevents activation or absorption of the first therapeutic agent. In some embodiments, the first therapeutic agent is delivered to an olfactory region of the subject, and the second therapeutic agent improves delivery of the first therapeutic agent to the olfactory region.

In some embodiments, the upper fluid comprises a sampling fluid which collects a biological material from the olfactory region of the nasal cavity. In some embodiments, the olfactory region of the nasal cavity is an olfactory cleft. In some embodiments, the method additionally comprises analyzing the sample fluid to evaluate the collected biological material.

In some embodiments, the lower fluid forms a capillary bridge at a lower aspect of an olfactory cleft of the nasal cavity. In some embodiments, the capillary bridge contacts opposing sides of an olfactory region of the subject's nasal cavity, and supports a coating of the formulation about the olfactory cleft. In some embodiments, the upper fluid is concentrated along an underside of a cribriform plate of the nasal cavity.

In some embodiments, the upper fluid and the lower fluid are delivered simultaneously. In some embodiments, the formulation is delivered as a homogeneous formulation which separates after delivery. In some embodiments, the upper fluid and the lower fluid form separate layers within about 1, 2, 3, 4, 5, 6, 7, 8, 9, 10, 12, 14, 16, 18, 20, 25, 30, 40, 50, or 60 seconds from delivery. In some embodiments, the formulation separates in response to an intranasal environmental factor or intranasal environmental conditions. In some embodiments, the environmental factor or environmental conditions comprises a pH, a temperature, a concentration of a biological material, a concentration of an enzyme, or combination thereof. In some embodiments, the formulation is delivered as a well-mixed heterogeneous formulation which forms an upper layer and a lower layer after delivery. In other embodiments, the formulation is delivered as a homogenous formulation which forms an upper layer and a lower layer after delivery.

In some embodiments, the upper fluid and the lower fluid are delivered sequentially. In some embodiments, the upper fluid is delivered through a dispensing tip and the lower fluid purges a residual amount of the upper fluid from the dispensing tip, thereby reducing a residual loss of the upper fluid and/or improving dose repeatability.

Reducing residual loss of the upper fluid can reduce wasting of the upper fluid.

In some embodiments, the upper fluid is delivered through a dispensing tip and the lower fluid purges a residual amount of the upper fluid from the device, thereby reducing wasted upper fluid.

Wasted upper fluid can encompass a portion of the upper fluid that cannot be ejected out of the device and/or a portion of the upper fluid that cannot be delivered to the target region, for example, because of tailing-off of the liquid stream.

In some embodiments, the upper fluid is delivered through a dispensing tip and the lower fluid purges a residual amount of the upper fluid from the device, thereby reducing a tail-off phase.

As used herein, the term "tail-off phase" refers to a phrase in ejecting a liquid where the liquid stream exhibits fragmentation at the tail and breaking into smaller liquid segments that travel at a slower velocity than the primary stream. This can occur when, for example, the device used to eject the liquid loses energy towards the end of the ejection.

Reducing the tail-off phase can reduce off-target delivery.

When delivering a single fluid through a dispensing tip, the fluid stream can be disrupted at the tail of the stream, and the cohesion of the ejected stream can be disturbed. It is demonstrated herein that when the formulation configured to form the upper fluid and the lower fluid is delivered through the dispensing tip, the presence of the ejected lower fluid minimizes the disruption to the tail of the upper fluid and preserves its cohesion.

In some embodiments, the upper fluid is delivered through a dispensing tip and the presence of the ejected lower fluid minimizes the disruption to the tail of the upper fluid and preserves its cohesion.

In some embodiments, the method includes orienting the subject in an upright orientation for a period of time after delivery of the formulation. In some embodiments, the period of time is greater than 1, 2, 3, 4, 5, 6, 7, 8, 9, 10, 15, 30, 45, 60, 75, 90, 105, 120, 150, or 180 minutes. In some embodiments, the method includes orienting the subject in an orientation such that contact between the upper fluid and an olfactory cleft of the subject is maximized. For example, in some embodiments, the subject's head may be oriented at an angle of about 5°, about 10°, about 15°, about 20°, about 25°, about 30°, about 35°, about 40°, or about 45° forward or backwards from an upright orientation.

In some embodiments, the method includes a priming step prior to delivery of the formulation wherein the upper fluid is primed from a fluid reservoir into a priming region prior to delivery. The priming region may comprise a shot chamber, a nozzle or cannula barrel, a dispensing tip, or a combination thereof. In some embodiments, the priming step may be accomplished at a speed selected to avoid subjecting the upper fluid to shear forces damaging to the therapeutic agent. In some embodiments, the lower fluid is primed into the dispensing tip and then delivered from the dispensing tip due to pressure exerted by the lower fluid. In some embodiments, the volume of the upper fluid primed into the dispensing tip is the entire volume of the upper fluid delivered. In other embodiments, the volume of the upper fluid primed into the dispensing tip is a fraction of the entire volume of the upper fluid delivered.

In some embodiments, a volume of about 25 μL to about 150 μL of either the upper fluid or the lower fluid is delivered to the nasal cavity. In some embodiments the volume of either the upper fluid or the lower fluid delivered to the nasal cavity is about 25 μL to about 50 μL, about 25 μL to about 75 μL, about 25 μL to about 100 μL, about 25 μL to about 125 μL, about 25 μL to about 150 μL, about 50 μL to about 75 μL, about 50 μL to about 100 μL, about 50 μL to about 125 μL, about 50 μL to about 150 μL, about 75 μL to about 100 μL, about 75 μL to about 125 μL, about 75 μL to about 150 μL, about 100 μL to about 125 μL, about 100 μL to about 150 μL, or about 125 μL to about 150 μL including increments therein.

In some embodiments, a total volume of the formulation delivered to the nasal cavity is about 25 μL to about 150 μL. In some embodiments, a total volume of the formulation delivered to the nasal cavity is about 25 μL to about 50 μL, about 25 μL to about 75 μL, about 25 μL to about 100 μL, about 25 μL to about 125 μL, about 25 μL to about 150 μL, about 50 μL to about 75 μL, about 50 μL to about 100 μL, about 50 μL to about 125 μL, about 50 μL to about 150 μL, about 75 μL to about 100 μL, about 75 μL to about 125 μL, about 75 μL to about 150 μL, about 100 μL to about 125 μL, about 100 μL to about 150 μL, or about 125 μL to about 150 μL including increments therein. In some embodiments, a total volume of the formulation delivered to the nasal cavity corresponds to a volume of the olfactory cleft, such that the formulation is able to partially or completely fill the olfactory cleft without waste of excess formulation.

In one aspect is a method of delivering a formulation to a nasal cavity of a subject, the method comprising: delivering a formulation to the olfactory region of the nasal cavity, the formulation configured to form: an upper fluid comprising a therapeutic agent; and a lower fluid, immiscible with the upper fluid at intranasal environmental conditions and having a greater density than that of the upper fluid; wherein one or more volumes of the formulation delivered to the olfactory region of the nasal cavity each form an upper layer comprising the upper fluid and a lower layer comprising the lower fluid, thereby concentrating the upper fluid against the olfactory region of the nasal cavity and delivering the therapeutic agent to the olfactory region of the nasal cavity.

In one aspect is a method of collecting biological material from an olfactory region of a subject, the method comprising: delivering a formulation to the olfactory region, the formulation configure to form: an upper fluid; and a lower fluid, immiscible with the upper fluid at intranasal environmental conditions and having a greater density than that of the upper fluid; wherein one or more volumes of the formulation delivered to the olfactory region of the nasal cavity each form an upper layer comprising the upper fluid and a lower layer comprising the lower fluid, thereby concentrating the upper fluid against the olfactory region; and withdrawing a portion of the formulation and the biological material captured therein, thereby collecting the biological material. In some embodiments, the method additionally comprises fractionation of the collected sampling fluid to help concentrate the biological material, or analyte, from the total volume of fluids ejected and retrieved for biomarker sampling.

In one aspect is a formulation for intranasal delivery, configured to form: an upper fluid; and a lower fluid, immiscible with the upper fluid at intranasal environmental conditions and having a greater density than that of the upper fluid; wherein at intranasal environmental conditions one or more volumes of the formulation each form an upper layer comprising the upper fluid and a lower layer comprising the lower fluid. In some embodiments, the formulation includes a therapeutic agent which is preferentially soluble in upper fluid. In some embodiments, the formulation includes a second therapeutic agent which is preferentially soluble in the lower fluid. In some embodiments, the formulation includes a therapeutic agent which is at least about 5%, at least about 10%, at least about 15%, at least about 20%, at least about 30%, at least about 40%, at least about 50%, at least about 60%, at least about 70%, at least about 80%, at least about 90%, at least about 100%, at least about 120%, at least about 140%, at least about 160%, at least about 180%, at least about 200%, at least about 250%, at least about 300%, at least about 350%, at least about 400%, at least about 450%, at least about 500%, at least about 600%, at least about 700%, at least about 800%, at least about 900%, at least about 1000%, at least about 1200%, at least about 1400%, at least about 1600%, at least about 1800%, at least about 2000%, at least about 2500%, at least about 3000%, at least about 3500%, at least about 4000%, at least about 4500%, at least about 5000%, at least about 6000%, at least about 7000%, at least about 8000%, at least about 9000%, at least about 10,000%, at least about 20,000%, at least about 40,000%, at least about 60,000%, at least about 80,000%, or at least about 100,000% more soluble in the upper fluid than in the lower fluid. In other embodiments, the formulation comprises a second therapeutic agent which is preferentially soluble in the lower fluid. In some embodiments, the formulation includes a therapeutic agent which is at least about 5%, at least about 10%, at least about 15%, at least about 20%, at least about 30%, at least about 40%, at least about 50%, at least about 60%, at least about 70%, at least about 80%, at least about 90%, at least about 100%, at least about 120%, at least about 140%, at least about 160%, at least about 180%, at least about 200%, at least about 250%, at least about 300%, at least about 350%, at least about 400%, at least about 450%, at least about 500%, at least about 600%, at least about 700%, at least about 800%, at least about 900%, at least about 1000%, at least about 1200%, at least about 1400%, at least about 1600%, at least about 1800%, at least about 2000%, at least about 2500%, at least about 3000%, at least about 3500%, at least about 4000%, at least about 4500%, at least about 5000%, at least about 6000%, at least about 7000%, at least about 8000%, at least about 9000%, at least about 10,000%, at least about 20,000%, at least about 40,000%, at least about 60,000%, at least about 80,000%, or at least about 100,000% more soluble in the lower fluid than in the upper fluid.

In some embodiments, the formulation comprises one or more therapeutic agents. In some embodiments, each therapeutic agent is independently selected from the group consisting of a drug, a small molecule drug, a large molecule drug, a biologic, a peptide, a protein, a nucleic acid, a monoclonal antibody, an oligonucleotide, a vaccine, a stem cell, a gene therapy agent, a cell therapy agent, and a nanoparticle.

In some embodiments, the upper fluid and the lower fluid are both liquids at intranasal environmental conditions. In some embodiments, the upper fluid is a gas at intranasal environmental conditions and the lower fluid is a liquid at intranasal environmental conditions. In some embodiments, at least one of the upper fluid and the lower fluid comprises water, glycerin, a saline solution, or an aqueous solution. In some embodiments, at least one of the upper fluid and the lower fluid comprises an organic oil, sesame oil, cottonseed oil, soybean oil, coconut oil, or a combination thereof. In some embodiments, at least one of the upper fluid and the lower fluid is hydrophobic. In some embodiments, at least one of the upper fluid and the lower fluid is hydrophilic.

In some embodiments, the lower fluid has a higher viscosity than the upper fluid. For example, in some embodiments, the lower fluid has a viscosity at least about 1%, at least about 2%, at least about 3%, at least about 4%, at least about 5%, at least about 6%, at least about 7%, at least about 8%, at least about 9%, at least about 10%, at least about 12%, at least about 14%, at least about 16%, at least about 18%, at least about 20%, at least about 22%, at least about 24%, at least about 26%, at least about 28%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 120%, at least about 140%, at least about 160%, at least about 180%, at least about 200%, at least about 250%, at least about 300%, at least about 350%, at least about 400%, at least about 450%, at least about 500%, at least about 600%, at least about 700%, at least about 800%, at least about 900%, at least about 1000%, at least about 1200%, at least about 1400%, at least about 1600%, at least about 1800%, at least about 2000%, at least about 2500%, at least about 3000%, at least about 3500%, at least about 4000%, at least about 4500%, at least about 5000%, at least about 6000%, at least about 7000%, at least about 8000%, at least about 9000%, at least about 10,000%, at least about 20,000%, at least about 40,000%, at least about 60,000%, at least about 80,000%, or at least about 100,000% greater than that of the upper fluid.

In some embodiments, the lower fluid has a higher surface tension than the upper fluid. For example, in some embodiments, the lower fluid has a surface tension that is at least about 1%, at least about 2%, at least about 3%, at least about 4%, at least about 5%, at least about 6%, at least about 7%, at least about 8%, at least about 9%, at least about 10%, at least about 12%, at least about 14%, at least about 16%, at least about 18%, at least about 20%, at least about 22%, at least about 24%, at least about 26%, at least about 28%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 120%, at least about 140%, at least about 160%, at least about 180%, at least about 200%, at least about 250%, at least about 300%, at least about 350%, at least about 400%, at least about 450%, at least about 500%, at least about 600%, at least about 700%, at least about 800%, at least about 900%, or at least about 1000% greater than the upper fluid.

In some embodiments, the formulation comprises a mucoadhesive agent. In some embodiments, the formulation comprises a surfactant. In some embodiments, the formulation is configured to form an emulsion, a micelle, a vesicle, or a liposome. In some embodiments, the formulation is configured to form: an upper layer comprising the upper fluid; a lower layer comprising the lower fluid; and an emulsion, a micelle, a vesicle, or a liposome, wherein the emulsion, micelle, vesicle, or liposome is preferentially distributed in the upper layer.

In some embodiments, the formulation is substantially free of surfactants and emulsifiers. In some embodiments, the formulation is substantially free of mucoadhesive agents. In some embodiments, the formulation is not configured to form an emulsion, a micelle, a vesicle, or a liposome. In some embodiments, at least one of the upper fluid and the lower fluid is thixotropic or shear thickening.

In some embodiments, the volume ratio of the upper fluid and the lower fluid is about 20:1, about 10:1, about 9:1, about 8:1, about 7:1, about 6:1, about 5:1, about 4:1, about 3:1, about 2:1, 1.9:1, about 1.8:1, about 1.7:1, about 1.6:1, about 1.5:1, about 1.4:1, about 1.3:1, about 1.2:1, about 1.1:1, about 1:1, about 1:1.1, about 1:1.2, about 1:1.3, about 1:1.4, about 1:1.5, about 1:1.6, about 1:1.7, about 1:1.8, about 1:1.9, about 1:2, about 1:3, about 1:4, about 1:5, about 1:6, about 1:7, about 1:8, about 1:9, about 1:10, or about 1:20.

In some embodiments, the lower fluid is at least about 1%, at least about 2%, at least about 3%, at least about 4%, at least about 5%, at least about 6%, at least about 7%, at least about 8%, at least about 9%, at least about 10%, at least about 12%, at least about 14%, at least about 16%, at least about 18%, at least about 20%, at least about 22%, at least about 24%, at least about 26%, at least about 28%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% more dense than the upper fluid.

In some embodiments, at least one of the upper fluid and the lower fluid has a viscosity of less than about 0.5, less than about 0.6, less than about 0.7, less than about 0.8, less than about 0.9, less than about 1, less than about 10, less than about 25, less than about 50, less than about 75, less than about 100, less than about 250, less than about 500, less than about 750, less than about 1000, less than about 1250, less than about 1500, less than about 1750, less than about 2000, less than about 2250, less than about 2500, less than about 2750, or less than about 3000 centipoise (cP).

In some embodiments, at least one of the upper fluid and the lower fluid has a viscosity of at least about 0.5, at least about 0.6, at least about 0.7, at least about 0.8, at least about 0.9, at least about 1, at least about 10, at least about 25, at least about 50, at least about 75, at least about 100, at least about 250, at least about 500, at least about 750, at least about 1000, at least about 1250, at least about 1500, at least about 1750, at least about 2000, at least about 2250, at least about 2500, at least about 2750, or at least about 3000 centipoise (cP).

In one aspect is a device for delivery of a formulation to an olfactory region of a nasal cavity, the device comprising: one or more fluid reservoirs configured to contain a formulation configured to form: an upper fluid; and a lower fluid immiscible with the upper fluid at intranasal environmental conditions and having a greater density than that of the upper fluid; wherein at intranasal environmental conditions one or more volumes of the formulation each form an upper layer comprising the upper fluid and a lower layer comprising the lower fluid; a dispensing tip for delivering the formulation to the olfactory region, wherein the dispensing tip is coupled with the one or more fluid reservoirs; and a dispensing mechanism for exerting pressure on the upper fluid and on the lower fluid such that the upper fluid and the lower fluid flow through the dispensing tip, thereby dispensing the formulation to the olfactory region. In some embodiments, the upper fluid comprises a therapeutic agent. In some embodiments, the therapeutic agent is preferentially soluble in the upper fluid. In some embodiments, a second therapeutic agent is preferentially soluble in the lower fluid.

In some embodiments, the device further comprises a coupling member, the coupling member coupling the dispensing tip with the one or more fluid reservoirs. In some embodiments, the coupling member is configured to be movable within the one or more fluid reservoirs along a central axis running vertically through the one or more fluid reservoirs. In some embodiments, the dispensing member is configured to exert pressure on the movable coupling member, thereby causing the upper fluid to flow through the dispensing tip. In some embodiments, the coupling member comprises a self-healing rubber.

In some embodiments, the upper fluid and the lower fluid are separated by a separating member in the one or more fluid reservoirs. In some embodiments, the separating member is configured to be movable within the one or more fluid reservoirs along a central axis running vertically through the one or more fluid reservoirs. In some embodiments, the separating member comprises a pre-punctured hole.

Figures 9A, 9B, 9C:
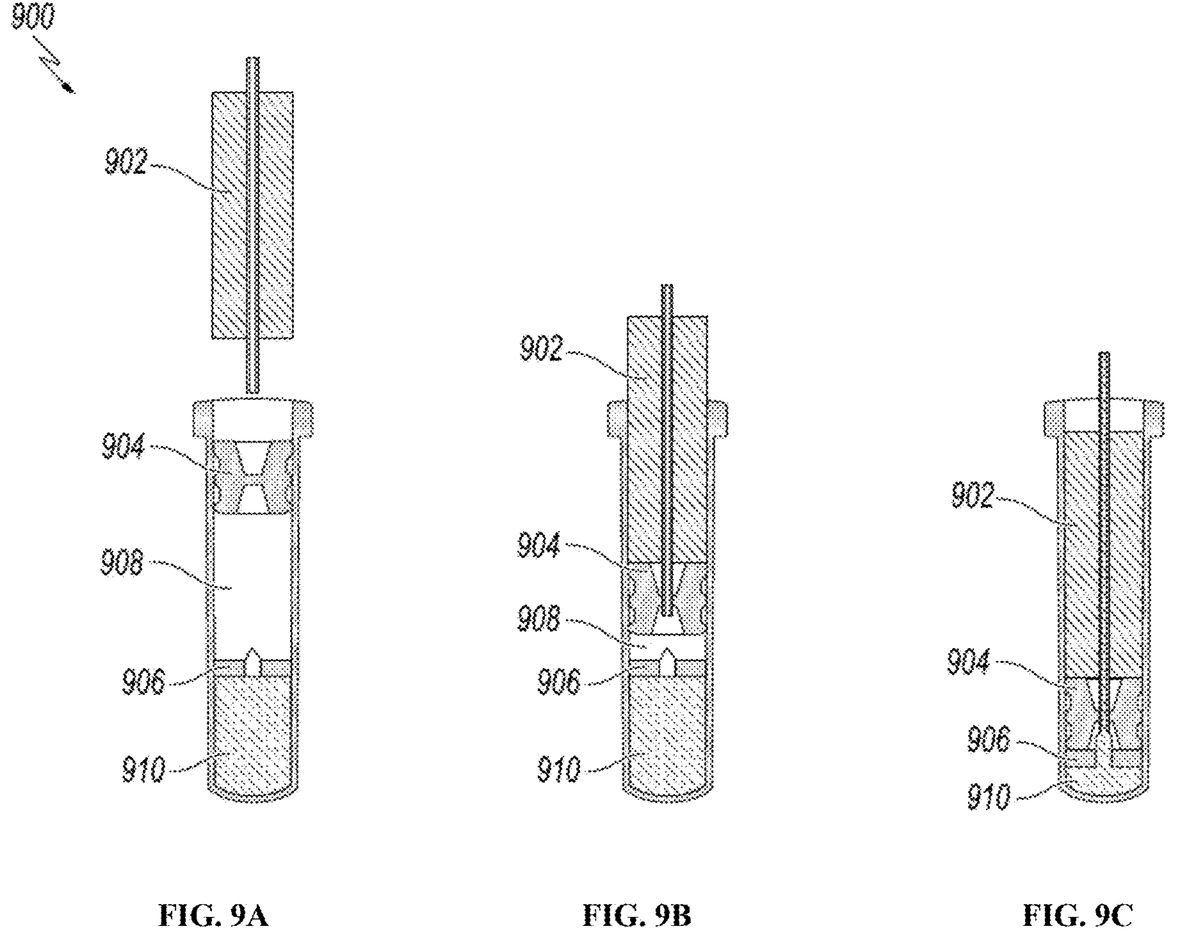
FIGS. 9A-9C depict delivery of a two-fluid formulation according to some embodiments.

Referring to FIGS. 9A-9C. These figures illustrate a device 900 according to certain embodiments of the present disclosure. The device 900 comprises one fluid reservoir. The fluid reservoir comprises a coupling member 904, which is couplable with a dispensing tip 902. The fluid reservoir can contain an upper fluid 908 and a lower fluid 910. The upper fluid 908 and the lower fluid 910 can be separated by a separating member 906. The separating member 906 can be a membrane. In some embodiments, the separating membrane comprises a pre-punctured hole. In FIG. 9B, the dispensing tip 902 is inserted into the coupling member 904. Pressure exerted onto the coupling member 904 causes the coupling member 904 to move along the fluid reservoir, displacing the upper fluid 908 and causing the upper fluid 908 to flow through the dispensing tip 902 out of the fluid reservoir. As the coupling member 904 reaches the separating member 906, the coupling member 904 and the separating member 906 move together along the fluid reservoir, causing the lower fluid 910 to flow through the pre-punctured hole and the dispensing tip 902 (FIG. 9C).

In some embodiments, the upper fluid is configured to deliver the therapeutic agent to the nasal cavity and the lower fluid is configured to increase a residence time of the therapeutic agent within the nasal cavity. In some embodiments, the upper fluid is configured to deliver the therapeutic agent to an olfactory cleft of the nasal cavity and the lower fluid is configured to at least partially obstruct, or fully obstruct a lower aspect of the olfactory cleft. In some embodiments, the olfactory region comprises an olfactory cleft. In some embodiments, the device dispenses a bolus of the formulation with an ejection profile selected to contact opposing sides of an olfactory cleft to at least partially fill the olfactory cleft, and support the upper fluid above the resulting capillary bridge.

In some embodiments, the dispensing mechanism is configured to dispense the upper fluid and the lower fluid sequentially. In some embodiments, the dispensing mechanism is configured to dispense the upper fluid first, to deliver a therapeutic agent to the nasal cavity, and the lower fluid second, to purge a residual amount of the upper fluid from the device or from one or more components of the device, such as the dispensing tip, a fluid reservoir, or any other component contacted by the upper fluid. In some embodiments, the dispensing mechanism is configured to dispense the upper fluid and the lower fluid simultaneously.

Figure 1D:
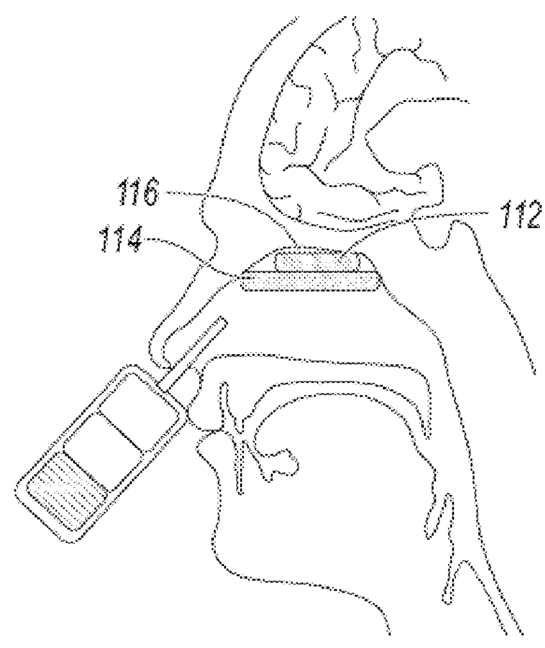
FIG. 1D is an illustration of the two fluids remaining separated at the olfactory cleft after sequential delivery.

FIGS. 1A-1D depict an example device 100 according to some embodiments. The device 100 comprises a dispensing tip 102, an upper reservoir 108, a lower reservoir 110, and a device enclosure 104. An upper fluid 112 is stored in the upper reservoir 108, and a lower fluid 114 is stored in the lower reservoir 110. In some embodiments, the device 100 further comprises a dispensing mechanism 106 for sequential delivery of the upper fluid 112 and the lower fluid 114. In some embodiments, sequential delivery of the upper fluid 112 and the lower fluid 114 results in the upper fluid 112 at least partially filling the olfactory cleft 116 and the lower fluid 114 supporting Fluid 1 (FIG. 1D).

Figure 2A:
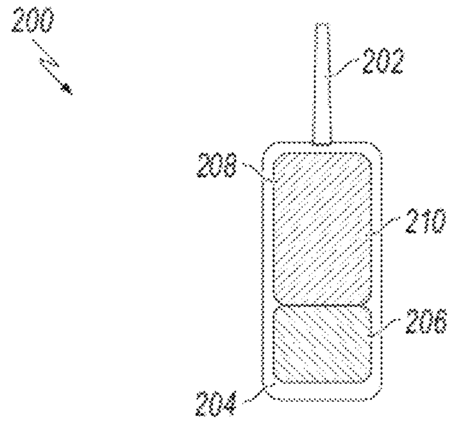
FIG. 2A depicts a device for intranasal delivery of a two-fluid formulation, wherein the fluids are stored in the same reservoir within the device.
Figure 2B:
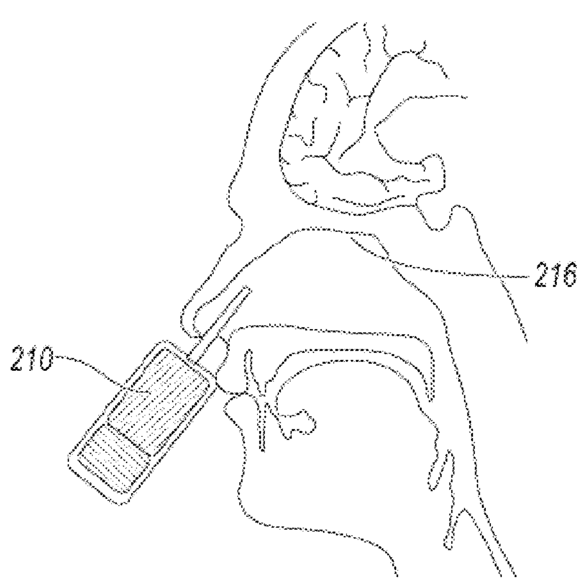
FIG. 2B is an illustration of the device inserted into a nasal cavity of the subject for olfactory delivery.
Figure 2C:
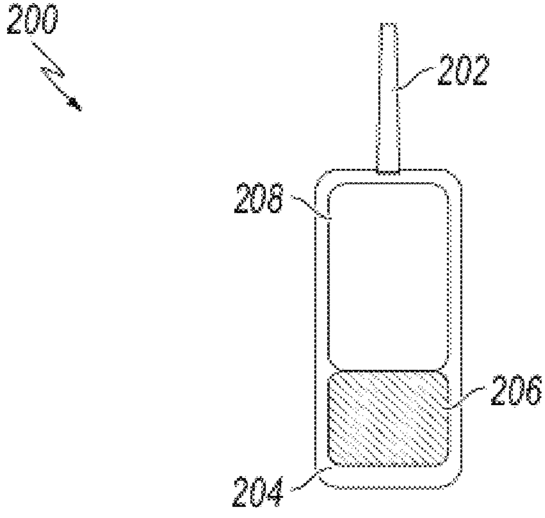
FIG. 2C depicts the device shown in FIG. 2A, after simultaneous delivery of the two fluids, which then separate at the olfactory cleft.
Figure 2D:
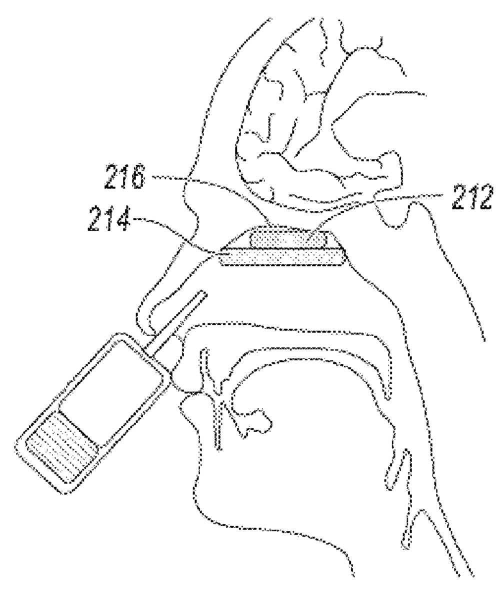
FIG. 2D is an illustration of the two fluids separated at the olfactory cleft after simultaneous delivery.

FIGS. 2A-2D depict an example device 200 according to some embodiments. The device 200 comprises a dispensing tip 202, a device enclosure 204, and a single reservoir 208. An upper fluid 212 and a lower fluid 214 are stored in the single reservoir 208 as a mixture 210. In some embodiments, the mixture 210 is a heterogeneous mixture that can be separated into the upper fluid 212 and the lower fluid 214 upon storage or upon delivery. In some embodiments, the mixture 210 is a homogeneous mixture. In some embodiments, the device 200 further comprises a dispensing mechanism 206 for simultaneous delivery of the upper fluid 212 and the lower fluid 214. In some embodiments, the upper fluid 212 and the lower fluid 214 separate at the olfactory cleft 216 after simultaneous delivery (FIG. 2D).

In some embodiments, the device comprises a single fluid reservoir for storage of the upper fluid and the lower fluid. In some embodiments, the upper fluid and the lower fluid are stored within a single fluid reservoir. In some embodiments, the fluid reservoir is configured to be pressurized such that the upper fluid and the lower fluid are stored as a homogenous mixture which separates after delivery of the homogenous mixture. In some embodiments, the fluid reservoir is configured to store the upper fluid and the lower fluid as stacked layers. In some embodiments, the device additionally comprises a viewing window to allow for evaluation of the mixing or layering of the two fluids within the single fluid reservoir. For example, one or both of the upper and lower fluids may be colored to provide for easer visualization of the formulation through the viewing window. In some embodiments, the upper layer comprises a first color, the lower layer comprises a second color, and a homogeneous mixture of the formulation comprises a third color.

In some embodiments, the single fluid reservoir has an exit port positioned such that when the device is held in a specified orientation during dispensing, the upper fluid is dispensed before the lower fluid. In some embodiments, the exit port is positioned away from a central axis running vertically through the fluid reservoir when the device is in an upright orientation (i.e. such that a long central axis of the device is vertical). In some embodiments, the central axis is an axis of rotational symmetry of the fluid reservoir. In some embodiments, positioning the exit port away from the central axis allows for delivery of all of the upper fluid from the single fluid reservoir prior to delivery of the lower fluid, and avoids trapping a residual amount of the upper fluid within the fluid reservoir, even if the fluids are dispensed while the device is oriented at an angle from the upright orientation.

In some embodiments, the device comprises separate fluid reservoirs for the separate storage of the upper fluid and the lower fluid. In some embodiments, the upper fluid and the lower fluid are stored within separate fluid reservoirs. In some embodiments, the device additionally comprises a blending mechanism for mixing the upper fluid and the lower fluid prior to dispensing.

In some embodiments, the device additionally comprises a damping mechanism configured to control dispensing of the two fluids. In some embodiments, the damping mechanism is a position dependent damping mechanism. In some embodiments, the damping mechanism is a two-stage position dependent damping mechanism, wherein the first stage is more strongly damped than the second stage. In some embodiments, the second stage is more strongly damped than the first stage. In some embodiments, the damping mechanism is configured to provide first stage damping during dispensing of the upper fluid and second stage damping during dispensing of the lower fluid. In some embodiments, the damping mechanism is configured to limit shear forces to the upper fluid during ejection, so as to minimize damage to the therapeutic agent.

In some embodiments, the damping mechanism is an internal damping mechanism configured to use the lower fluid as a damping fluid. In some embodiments, the damping mechanism is an external damping mechanism configured to use a separate damping fluid in an external dashpot chamber. In some embodiments, the separate damping fluid has a viscosity of at least about 1, at least about 10, at least about 25, at least about 50, at least about 75, at least about 100, at least about 250, at least about 500, at least about 750, at least about 1000, at least about 1250, at least about 1500, at least about 1750, at least about 2000, at least about 2250, at least about 2500, at least about 2750, or at least about 3000 centipoise (cP).

In some embodiments, the damping mechanism comprises a piston within a cylinder, wherein the cylinder has a change in diameter at a position along the length of the cylinder.

Figure 3A:
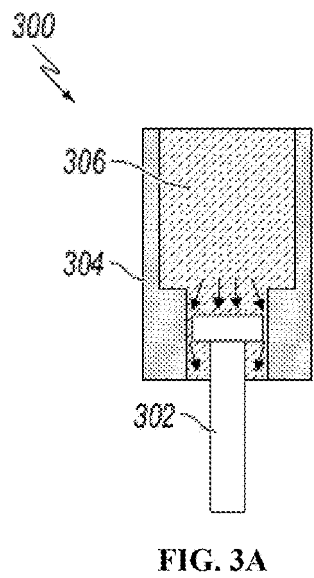
FIGS. 3A-3B depict a device for intranasal delivery having an external damping mechanism with a bore step change. A smaller bore between the piston and cylinder wall provides more resistance to motion (FIG. 3A) and a larger bore between the piston and cylinder wall provides less resistance to motion (FIG. 3B). The arrows represent the fluid flow path.
Figure 3B:
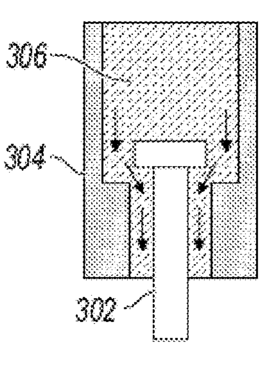

FIGS. 3A-3B depict an example device 300 comprising a damping mechanism in some embodiments. The device 300 comprises a piston 302 and a cylinder wall 304. A smaller bore between the piston 302 and the cylinder wall 304 provides more resistance to motion of fluid 306 (FIG. 3A) and a larger bore between the piston 302 and the cylinder wall 304 provides less resistance to motion of fluid 306 (FIG. 3B).

Figure 4A:
FIGS. 4A-4C depict a device for intranasal delivery having an external damping mechanism with occluding holes. Rods in the cylinder have various diameters and/or diameter changes along their length (FIG. 4A) and the flow path decreases or increases as the holes in the piston head are opened or closed by the rods (FIGS. 4B-4C).
Figure 4A:
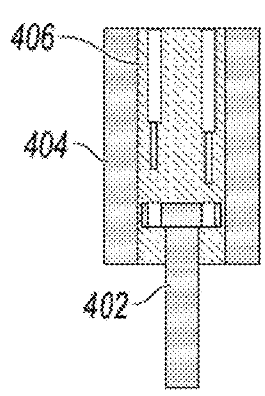
Figure 4B:
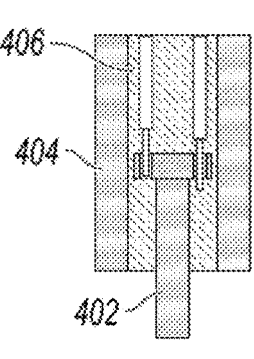
Figure 4C:
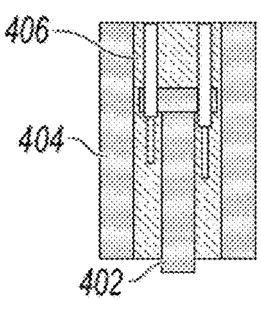

Referring to FIGS. 4A-4C, which depict an example device 400 comprising a damping mechanism in some embodiments. In some embodiments, the damping mechanism comprises a piston 402 within a cylinder 404, wherein the piston 402 comprises a piston head having one or more holes for one or more rods to pass through, and wherein the one or more rods have variable diameters. In some embodiments, the one or more rods have one or more diameter changes along their length and the flow path of fluid 406 decreases or increases as the holes in the piston head are opened or closed by the rods.

In some embodiments, the damping mechanism comprises a fixed orifice plate within one of the fluid reservoirs and one or more rods configured to pass through one or more holes in the orifice plate. In some embodiments, the damping mechanism comprises a movable orifice plate within one of the fluid reservoirs and one or more static rods configured to pass through one or more holes in the movable orifice plate.

Referring to FIGS. 5A-5C, which depict an example device 500 comprising a damping mechanism in some embodiments. In some embodiments, the damping mechanism comprises a static orifice plate with holes 510 that is fixed within syringe walls 504. In some embodiments, the damping mechanism comprises a syringe plunger 502 with rods 512 having variable diameter attached to the syringe plunger 502. The flow path decreases or increases as holes in the static orifice plate 510 are opened or closed by the rods 512. In some embodiments, the static orifice plate 510 is immersed in a lower fluid 508 that is heavier. In some embodiments, the static orifice plate 510 is immersed in an upper fluid 506 that is lighter.

Referring to FIGS. 6A-6C, which depict an example device 600 comprising a damping mechanism in some embodiments. In some embodiments, the damping mechanism comprises an orifice plate with holes 610 within the lower fluid 608, and static rods 612 within the upper fluid 606. The orifice plate with holes 610 is connected to a syringe plunger 602 through a fixed member 614 and the static rods 612 are connected to the syringe. As the syringe plunger 602 is pushed through the syringe along the inside of the syringe walls 604, the orifice plate with holes 610 travels with the syringe plunger 602 towards the static rods 612, and the flow path decreases or increases as holes in the orifice plate 610 are opened or closed by the rods 612. The orifice plate with holes 610 can be within the upper fluid 606 or the lower fluid 608.

In some embodiments, the damping mechanism comprises a fixed orifice plate within one of the fluid reservoirs and one or more dumbbell-shaped pins configured to pass through one or more holes in the orifice plate.

In some embodiments, the damping mechanism comprises a movable orifice plate within one of the fluid reservoirs and one or more rods configured to pass through one or more holes in the orifice plate.

Referring to FIGS. 7A-7C, which depict an example device 700 comprising a damping mechanism in some embodiments. In some embodiments, the damping mechanism comprises a fixed orifice plate comprising one or more holes 710, and one or more pins 712 configured to be movable through the one or more holes. In some embodiments, the pin is dumbbell shaped. The fixed orifice plate comprising one or more holes 710 can be within an upper fluid 706 or a lower fluid 708. In some embodiments, the device 700 further comprises a syringe plunger 702. As the syringe plunger 702 advances along a central axis of the syringe walls 704, the syringe plunger 702 knocks the one or more pins 712 from the orifice plate 710, increasing the flow path.

In some embodiments, the device comprises a lock-out mechanism configured to prevent dispensing if the device is in an undesirable orientation. For example, the lock-out mechanism may prevent dispensing if the device is in an orientation in which the lower fluid would be dispensed before the upper fluid is dispensed.

Definitions

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure can be described in the context of a single embodiment, the features can also be provided separately or in any suitable combination. Conversely, although the present disclosure can be described herein in the context of separate embodiments for clarity, the disclosure can also be implemented in a single embodiment.

Reference in the specification to "some embodiments," "an embodiment," "one embodiment" or "other embodiments" means that a feature, structure, or characteristic described in connection with the embodiments is included in at least some embodiments, but not necessarily all embodiments, of the present disclosure.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the disclosure can be used to achieve methods of the disclosure.

The term "about" or "approximately" as used herein when referring to a measurable value such as a parameter, an amount, a temporal duration, and the like, is meant to encompass variations of +/−10% or less from the specified value, insofar such variations are appropriate to perform in the present disclosure. It is to be understood that the value to which the modifier "about" or "approximately" refers is itself also specifically disclosed.

As used herein, the term "normal temperature and pressure" or "NTP" refers to conditions of about 20° C. temperature and about one atm of pressure.

As used herein, the term "immiscible" refers to being incapable of attaining homogeneity. Miscibility may depend on environmental conditions. For example, a formulation may be miscible within a pressurized fluid reservoir, but immiscible at intranasal environmental conditions such as the conditions within an olfactory cleft.

The term "composition" or "compound" or "therapeutic" or "sampling compound" or "sampling fluid" is therapeutics, medicaments, drugs, small and large molecules, medicaments in liquid, powder, or gas form, or a combination thereof having a low, intermediate, or high viscosity. These may include various combinations of pharmaceutically acceptable excipients, odorants, or other additives, chemically or biologically derived.

The term "dual-density formulation" refers to a formulation separated into a denser or lower layer and a lighter or upper layer, or to a formulation configured to separate into a denser layer and a lighter layer under selected circumstances, such as NTP or when exposed to an intranasal environmental factor or intranasal environmental conditions. For example, the term "dual density formulation" could refer to an inhomogenous formulation with an upper layer and a lower layer, or to a homogenous formulation which separates into an upper layer and a lower layer after delivery into an intranasal cavity or exposure to NTP.

The term "intranasal environmental conditions" refers to the normal range of environmental conditions present within the intranasal cavity of a living subject. For example, intranasal environmental conditions include temperature, pressure, and humidity conditions within the normal ranges present within the intranasal cavity of a living subject.

The term "nasal cavity" comprises a vestibule, respiratory region, olfactory cleft, and a nasopharynx.

The term "trigger" refers to the part of the device that actuates the ejection mechanism, which in turn (through a variety of possible mechanism designs), delivers a compound from the device.

The term "turbinates" refers to superior turbinate, middle turbinate, or inferior turbinate, or a combination thereof.

Nasal Cavity: This is the large, air-filled space behind the nose, where air passes on its way to the throat during inhalation.

Internal Nasal Valve: This is the narrowest part of the nasal airway, located just beyond the nostril. It's formed by the edge of the nasal septum, the upper lateral cartilage, and the floor of the nose. The internal nasal valve plays a critical role in regulating airflow through the nose. The area of interest is superior (above) to this structure.

Nasal Septum: This is the thin wall of bone and cartilage that separates the right and left nostrils. It forms the medial (towards the middle) boundary of the region of interest.

Lateral Nasal Wall: This is the side wall of the nasal cavity, which is opposite to the nasal septum. It's a complex structure that includes the turbinates (long, curled bones that protrude into the nasal cavity) and the meatuses (grooves or channels between the turbinates). The lateral nasal wall forms the lateral (towards the side) boundary of the region of interest.

Middle and Superior Meatuses: These are the spaces within the nasal cavity located between the turbinates. The middle meatus is located beneath the middle turbinate and above the inferior turbinate, and the superior meatus is located beneath the superior turbinate. The region of interest encompasses parts of these spaces.

Nostrils (External Nares): These are the two openings of the nose where air enters.

Nasal Vestibule: The nasal vestibule is the most anterior part of the nasal cavity, just inside the nostrils. It is the area of the nose that protrudes outside the face predominantly. This area is lined with skin and contains hair follicles, and it acts as the initial filtering and warming area for inhaled air before it moves deeper into the nasal cavity. The nasal vestibule extends posteriorly to the nasal valve, which is the narrowest part of the nasal airway and located just beyond the nostril.

Nasal Septum: This is a thin wall made of bone and cartilage that separates the left and right sides of the nasal cavity.

Turbinates (Nasal Conchae): These are three pairs of bony projections (inferior, middle, and superior) covered in mucous membrane that protrude into the nasal cavity from the lateral walls. They increase the surface area of the nasal cavity, aiding in the warming, humidification, and filtration of inhaled air.

Meatuses: These are the spaces located between the turbinates. Each turbinate has a corresponding meatus underneath it (i.e., inferior, middle, and superior meatus).

Olfactory Region: This is a small area located at the top of the nasal cavity, where the sense of smell is located. In some embodiments, the olfactory region is an olfactory cleft.

EXAMPLES

Example 1 Dual Liquid Delivery Separated by a Physical Barrier

Dual liquid delivery from a single micro vial poses possible formulation, fill, and stability concerns. The liquids need to be carefully loaded and primed to prevent mixing prior to actuation. Stability and priming concerns could possibly be mitigated by adding a physical barrier between the two liquid volumes. Alternatively, the bottom volume could be an inert gas.

A prototype device was constructed to deliver and image two liquids being delivered from a single micro vial using this concept. The concept was tested with both gas and liquid loaded below the physical barrier.

FIG. 8 shows a target dose loaded on top, and empty volume loaded into the bottom. The bottom volume could be liquid or gas. A second stopper would be placed on the top of the upper dose (not pictured). The concept was tested with a bidose sized vial.

FIGS. 9A-9C illustrate a prototype where the separating barrier was created by puncturing a typical vial stopper with a small gauge needle. The self-healing rubber prevented the two liquids from mixing during filling and priming. Once the top stopper contacts the middle stopper, the two stopper begin to travel together. At this point the bottom volume can vent through the pre-punctured hole in the middle stopper. The bottom stopper is never physically punctured by the device during actuation.

FIG. 9A illustrates a pre-actuation vial with target liquid on top, and secondary liquid on bottom, separated by a physical valve membrane.

In FIG. 9B, the needle has punctured the top stopper. The top stopper is pressed by a needle shoulder, stopper translation displaces the dose and expels it from the device. The physical membrane restricts mixing at this stage.

Once the target dose has been completely displaced and ejected (FIG. 9C), the stopper contacts the physical membrane, and the two components slide simultaneously. As these components translate the pressure differential allows the purple membrane to open and the secondary dose to be displaced and delivered. The needle never physically punctures the purple membrane.

In single liquid delivery systems, a portion of the liquid often remains trapped in the internal volume downstream of the microvial. Once the microvial is emptied, there is no longer pressure to expel this residual fluid, causing it to remain within the device and not be delivered. On average, 90 μL of the loaded dose is lost as residuals within the device. Additionally, part of the liquid is released during a "tail-off phase" as the device's energy decreases towards the end of the spray, making it less likely for this portion to reach the intended target in the nose.

The dual liquid delivery has the potential to solve both these problems by delivering the entire target dose with significantly reduced device residuals, as the second liquid volume (bottom) replaces the target liquid volume (top) as the device residuals. Additionally, the any tail-off characteristics of spray as the device loses energy will only be seen in the secondary liquid.

Expelled doses were imaged with a grey-scale high speed camera.

Figure 10:
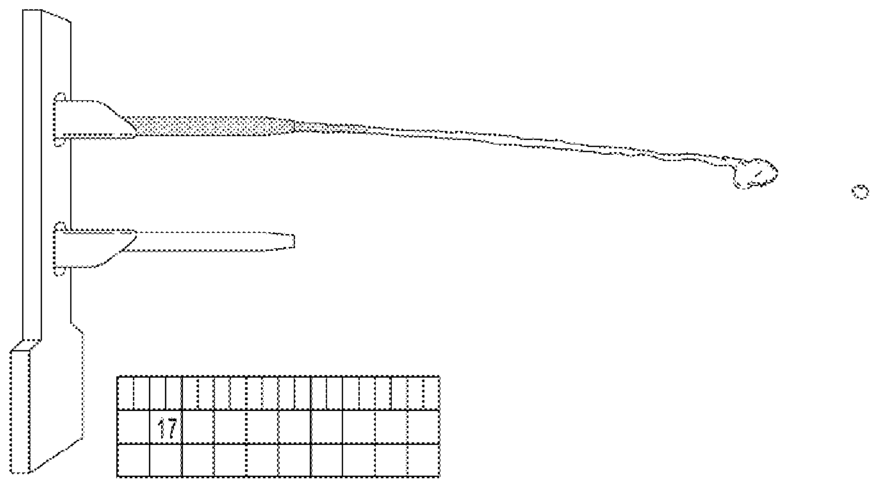
FIG. 10 is an image and an illustration of an expelled dose according to some embodiments.

100 μL of clear dose was loaded over the top of 140 μL non-clear dose with a stopper separating the two doses. It can be seen in FIG. 10 where the clear dose transitions to non-clear dose with no tail-off characteristic to the end of the clear (target, top) liquid delivery. It can also be concluded that a very high percentage of the clear liquid volume has been expelled from the device.

Figure 11:
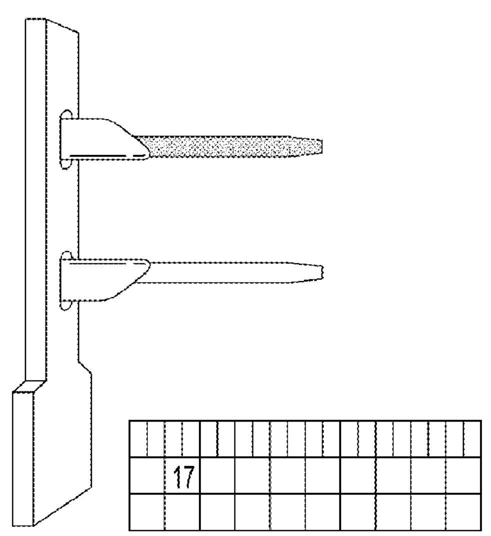
FIG. 11 is an image and an illustration of an end of spray according to some embodiments.

At end of spray the device residuals of the top cannula are from the bottom dose (FIG. 11).

Figure 12:
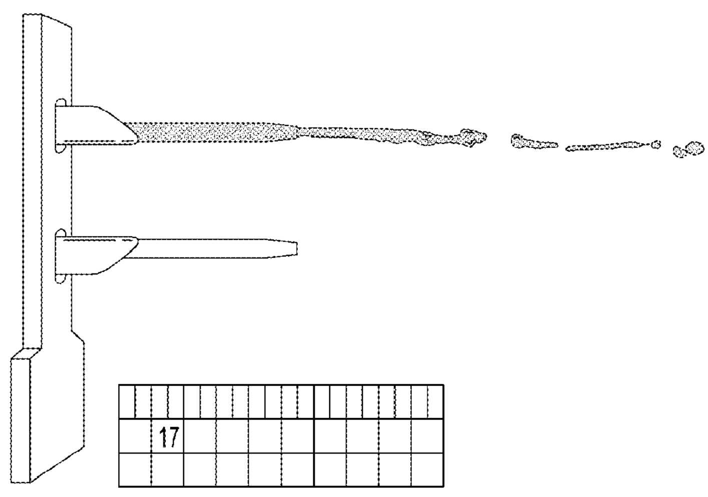
FIG. 12 is an image and an illustration of an initial spray according to some embodiments.

Delivery from a vial containing 160 μL loaded on top of the middle stopper, with air loaded below the middle stopper was also investigated. FIG. 12 shows an initial spray from the vial, FIG. 13 shows a mid-spray, and FIG. 14 shows an end spray.

Figure 13:
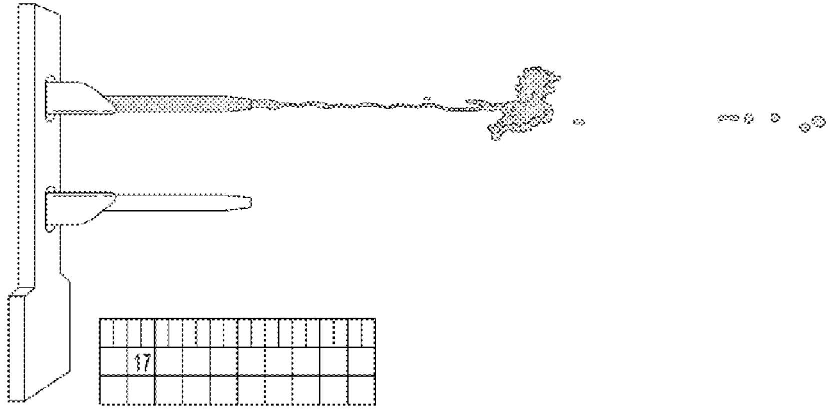
FIG. 13 is an image and an illustration of a mid-spray according to some embodiments.
Figure 14:
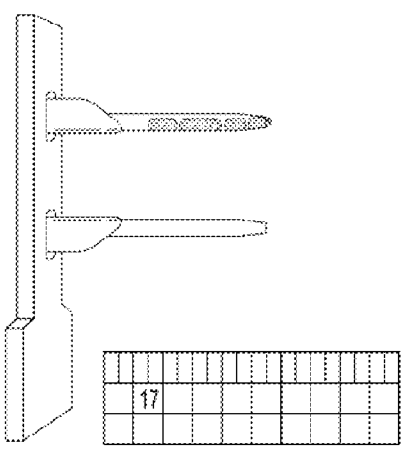
FIG. 14 is an image and an illustration of an end of spray according to some embodiments.

The mid-spray shown in FIG. 13 shows that the gas push accelerates into the back of the delivered dose. This gas push may provide a beneficial deposition mechanic, or reduce device residuals. Testing has shown a reduction in device residuals by as much as 60%. A gas push may be preferrable to a secondary pushing liquid due to drug stability and fill considerations for certain drugs.

Example 2 Dual Liquid Delivery Without a Physical Barrier

A prototype device was developed with a single fluid reservoir. Using this prototype, the tail-off behavior of a dose in single liquid delivery system was compared to that observed in a dual liquid delivery system.

Figure 15:
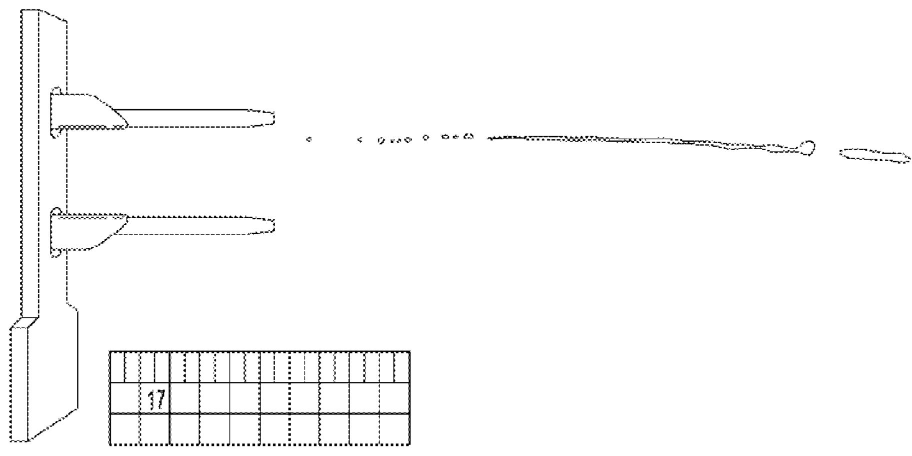
FIG. 15 is an image and an illustration illustrating the tail-off behavior of a dose in single liquid delivery system.

140 μL of clear dose was loaded into the reservoir of the prototype device and ejected. As illustrated in FIG. 15, the ejected dose displays a "tail-off" phase in which the stream exhibits fragmentation at the tail, breaking into smaller liquid segments and beads that travel at a slower velocity than the primary stream. The dose contained in this "tail-off" phase is less likely to reach the target destination than the primary stream of ejected dose.

For comparison, 140 μL of liquid, consisting of 60 μL of a clear dose and 80 μL of a non-clear, higher-density liquid, was loaded into the prototype delivery device. The density difference between the fluids was chosen to ensure natural separation into distinct upper and lower layers within the reservoir, with the dose forming the upper layer. The liquids were then ejected from the device.

Figure 16:
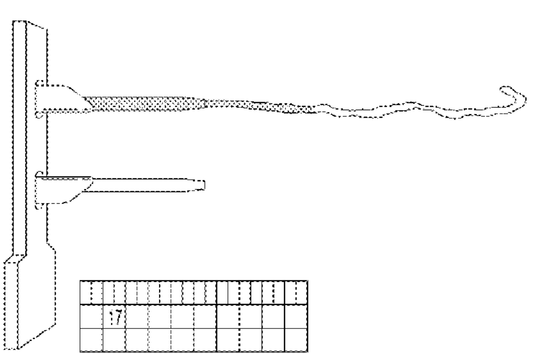
FIG. 16 is an image and an illustration illustrating absence of the tail-off phase in the upper fluid ejected from a dual density device according to some embodiments.

As shown in FIG. 16, the clear liquid does not exhibit a tail-off phase. Instead, the transition from the clear dose to the non-clear liquid occurs smoothly and without interruption in the ejected stream. The latter portion of the stream, following the transition, is composed entirely of the non-clear liquid. It is only this non-clear liquid that will experience tail-off behavior, while the entire clear dose remains intact in the primary ejection, reaching the targeted region of the nasal cavity.

ENUMERATED EMBODIMENTS

Enumerated Embodiment 1. A method of concentrating a fluid against an olfactory region of a nasal cavity of a subject, the method comprising:

- a. delivering a formulation to the olfactory region of the nasal cavity, the formulation configured to form:
  - i. an upper fluid; and
  - ii. a lower fluid, immiscible with the upper fluid at intranasal environmental conditions and having a greater density than that of the upper fluid;

wherein one or more volumes of the formulation delivered to the olfactory region of the nasal cavity each form an upper layer comprising the upper fluid and a lower layer comprising the lower fluid, thereby concentrating the upper fluid against the olfactory region of the nasal cavity.

Enumerated Embodiment 2. The method of any one of the enumerated embodiments, wherein to the olfactory region comprises an olfactory cleft of the nasal cavity.

Enumerated Embodiment 3. The method of any one of the enumerated embodiments, wherein the upper fluid comprises a therapeutic agent.

Enumerated Embodiment 4. The method of any one of the enumerated embodiments, wherein the therapeutic agent is preferentially soluble in the upper fluid, and wherein the formulation optionally comprises a second therapeutic agent which is preferentially soluble in the lower fluid.

Enumerated Embodiment 5. The method of any one of the enumerated embodiments, wherein the upper fluid delivers the therapeutic agent to the olfactory region of the nasal cavity, and the lower fluid increases a residence time of the therapeutic agent within the nasal cavity.

Enumerated Embodiment 6. The method of any one of the enumerated embodiments, wherein the upper fluid delivers the therapeutic agent to an olfactory cleft of the nasal cavity, and the lower fluid at least partially obstructs a lower aspect of an olfactory cleft of the nasal cavity.

Enumerated Embodiment 7. The method of any one of the enumerated embodiments, wherein the lower fluid comprises a therapeutic agent.

Enumerated Embodiment 8. The method of any one of the enumerated embodiments, wherein the upper fluid comprises a first therapeutic agent, preferentially soluble in the upper fluid, and the lower fluid comprises a second therapeutic agent, preferentially soluble in the lower fluid.

Enumerated Embodiment 9. The method of any one of the enumerated embodiments, wherein the first therapeutic agent is delivered to an olfactory region of the subject, and the second therapeutic agent affects a tissue so as to influence absorption of the first therapeutic agent.

Enumerated Embodiment 10. The method of any one of the enumerated embodiments, wherein the first therapeutic agent is delivered to an olfactory region of the subject, and the second therapeutic agent improves delivery of the first therapeutic agent to the olfactory region.

Enumerated Embodiment 11. The method of any one of the enumerated embodiments, wherein the upper fluid comprises a sampling fluid which collects a biological material from the olfactory region of the nasal cavity.

Enumerated Embodiment 12. The method of any one of the enumerated embodiments, wherein the olfactory region of the nasal cavity is an olfactory cleft.

Enumerated Embodiment 13. The method of any one of the enumerated embodiments, additionally comprising analyzing the sampling fluid to evaluate the collected biological material.

Enumerated Embodiment 14. The method of any one of the enumerated embodiments, wherein the lower fluid forms a capillary bridge at a lower aspect of an olfactory cleft of the nasal cavity.

Enumerated Embodiment 15. The method of any one of the enumerated embodiments, wherein the capillary bridge contacts opposing sides of an olfactory region of the subject's nasal cavity, and supports a coating of the formulation about the olfactory cleft.

Enumerated Embodiment 16. The method of any one of the enumerated embodiments, wherein the olfactory region of the nasal cavity comprises an underside of a cribriform plate of the nasal cavity.

Enumerated Embodiment 17. The method of any one of the enumerated embodiments, wherein the upper fluid and the lower fluid are delivered simultaneously.

Enumerated Embodiment 18. The method of any one of the enumerated embodiments, wherein the formulation is delivered as a homogenous formulation which separates after delivery.

Enumerated Embodiment 19. The method of any one of the enumerated embodiments, wherein the formulation separates into the upper fluid and the lower fluid within about 1, 2, 3, 4, 5, 6, 7, 8, 9, 10, 12, 14, 16, 18, 20, 25, 30, 40, 50, or 60 seconds from delivery.

Enumerated Embodiment 20. The method of any one of the enumerated embodiments, wherein the formulation separates into the upper fluid and the lower fluid in response to an intranasal environmental factor.

Enumerated Embodiment 21. The method of any one of the enumerated embodiments, wherein the environmental factor comprises a pH, a temperature, a concentration of a biological material, a concentration of an enzyme, or combination thereof.

Enumerated Embodiment 22. The method of any one of the enumerated embodiments, wherein the formulation is delivered as a well-mixed heterogenous formulation which forms an upper layer and a lower layer after delivery.

Enumerated Embodiment 23. The method of any one of the enumerated embodiments, wherein the upper fluid and the lower fluid are delivered sequentially.

Enumerated Embodiment 24. The method of any one of the enumerated embodiments, wherein the upper fluid is delivered through a dispensing tip and the lower fluid purges a residual amount of the upper fluid from the device, thereby reducing a residual loss of the upper fluid and improving dose repeatability.

Enumerated Embodiment 25. The method of one any of the enumerated embodiments, additionally comprising orienting the subject in an upright orientation for a period of time after delivery of the formulation.

Enumerated Embodiment 26. The method of any one of the enumerated embodiments, wherein the period of time is greater than 1, 2, 3, 4, 5, 6, 7, 8, 9, 10, 15, 30, 45, 60, 75, 90, 105, 120, 150, or 180 minutes.

Enumerated Embodiment 27. The method of any one of the enumerated embodiments, additionally comprising orienting the subject in an orientation such that contact between the upper fluid and an olfactory cleft of the subject is maximized.

Enumerated Embodiment 28. The method of any one of the enumerated embodiments, wherein a residence time of the formulation in the nasal cavity is at least about 1%, at least about 2%, at least about 3%, at least about 4%, at least about 5%, at least about 6%, at least about 7%, at least about 8%, at least about 9%, at least about 10%, at least about 12%, at least about 14%, at least about 16%, at least about 18%, at least about 20%, at least about 22%, at least about 24%, at least about 26%, at least about 28%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 120%, at least about 140%, at least about 160%, at least about 180%, at least about 200%, at least about 250%, at least about 300%, at least about 350%, at least about 400%, at least about 450%, at least about 500%, at least about 600%, at least about 700%, at least about 800%, at least about 900%, at least about 1000%, at least about 1200%, at least about 1400%, at least about 1600%, at least about 1800%, at least about 2000%, at least about 2500%, at least about 3000%, at least about 3500%, at least about 4000%, at least about 4500%, at least about 5000%, at least about 6000%, at least about 7000%, at least about 8000%, at least about 9000%, at least about 10,000%, at least about 20,000%, at least about 40,000%, at least about 60,000%, at least about 80,000%, or at least about 100,000% greater than a residence time of the upper fluid alone.

Enumerated Embodiment 29. The method of any one of the enumerated embodiments, additionally comprising a priming step prior to delivery of the formulation wherein the upper fluid is primed from a fluid reservoir into a priming region prior to delivery.

Enumerated Embodiment 30. The method of any one of the enumerated embodiments, wherein a volume of about 25 μL to about 150 μL of either the upper fluid or the lower fluid is delivered to the nasal cavity.

Enumerated Embodiment 31. The method of any one of the enumerated embodiments, wherein a total volume of the formulation delivered to the nasal cavity is about 25 μL to about 150 μL.

Enumerated Embodiment 32. A method of delivering a therapeutic agent to an olfactory region of a nasal cavity of a subject, the method comprising:

a. delivering a formulation to the olfactory region of the nasal cavity, the formulation configured to form:
   i. an upper fluid comprising a therapeutic agent; and
   ii. a lower fluid, immiscible with the upper fluid at intranasal environmental conditions and having a greater density than that of the upper fluid;

wherein one or more volumes of the formulation delivered to the olfactory region of the nasal cavity each form an upper layer comprising the upper fluid and a lower layer comprising the lower fluid, thereby concentrating the upper fluid against the olfactory region of the nasal cavity and delivering the therapeutic agent to the olfactory region of the nasal cavity.

Enumerated Embodiment 33. A method of collecting biological material from an olfactory region of a subject, the method comprising:

a. delivering a formulation to the olfactory region, the formulation configured to form:
   i. an upper fluid; and
   ii. a lower fluid, immiscible with the upper fluid at intranasal environmental conditions and having a greater density than that of the upper fluid;

wherein one or more volumes of the formulation delivered to the olfactory region of the nasal cavity each form an upper layer comprising the upper fluid and a lower layer comprising the lower fluid, thereby concentrating the upper fluid against the olfactory region; and b. withdrawing a portion of the formulation and the biological material captured therein, thereby collecting the biological material.

Enumerated Embodiment 34. A formulation for intranasal delivery, the formulation configured to form:

a. an upper fluid; and
b. a lower fluid, immiscible with the upper fluid at intranasal environmental conditions and having a greater density than that of the upper fluid;

wherein at intranasal environmental conditions, one or more volumes of the formulation each form an upper layer comprising the upper fluid and a lower layer comprising the lower fluid.

Enumerated Embodiment 35. The formulation of any one of the enumerated embodiments, additionally comprising a therapeutic agent which is preferentially soluble in the upper fluid, and optionally comprising a second therapeutic agent which is preferentially soluble in the lower fluid.

Enumerated Embodiment 36. The formulation of any one of the enumerated embodiments, wherein the therapeutic agent is selected from the group consisting of a drug, a small molecule drug, a large molecule drug, a biologic, a peptide, a protein, a nucleic acid, a monoclonal antibody, an oligonucleotide, a vaccine, a stem cell, a gene therapy agent, a cell therapy agent, and a nanoparticle.

Enumerated Embodiment 37. The formulation of any one of the enumerated embodiments, wherein the upper fluid and the lower fluid are both liquids at intranasal environmental conditions.

Enumerated Embodiment 38. The formulation of any one of the enumerated embodiments, wherein the lower fluid is a liquid at intranasal environmental conditions and the upper fluid is a gas at intranasal environmental conditions.

Enumerated Embodiment 39. The formulation of any one of the enumerated embodiments, wherein at least one of the upper fluid and the lower fluid comprises water, glycerin, a saline solution, or an aqueous solution.

Enumerated Embodiment 40. The formulation of any one of the enumerated embodiments, wherein at least one of the upper fluid and the lower fluid comprises an organic oil, sesame oil, cottonseed oil, soybean oil, coconut oil, or a combination thereof.

Enumerated Embodiment 41. The formulation of any one of the enumerated embodiments, wherein at least one of the upper fluid and the lower fluid is hydrophobic.

Enumerated Embodiment 42. The formulation of any one of the enumerated embodiments, wherein the lower fluid has a higher viscosity than the upper fluid.

Enumerated Embodiment 43. The formulation of any one of the enumerated embodiments, wherein the lower fluid has a higher surface tension than the upper fluid.

Enumerated Embodiment 44. The formulation of any one of the enumerated embodiments, wherein the formulation is substantially free of mucoadhesive agents.

Enumerated Embodiment 45. The formulation of any one of the enumerated embodiments, additionally comprising a surfactant.

Enumerated Embodiment 46. The formulation of any one of the enumerated embodiments, wherein the formulation is configured to form an emulsion, a micelle, a vesicle, or a liposome.

Enumerated Embodiment 47. The formulation of any one of the enumerated embodiments, wherein the formulation is configured to form:

a. an upper layer comprising the upper fluid;
b. a lower layer comprising the lower fluid; and
c. an emulsion, a micelle, a vesicle, or a liposome, wherein the emulsion, micelle, vesicle, or liposome is preferentially distributed in the upper layer.

Enumerated Embodiment 48. The formulation of any one of the enumerated embodiments, wherein the formulation is substantially free of surfactants and emulsifiers.

Enumerated Embodiment 49. The formulation of any one of the enumerated embodiments, wherein the formulation is not configured to form an emulsion, a micelle, a vesicle, or a liposome.

Enumerated Embodiment 50. The formulation of any one of the enumerated embodiments, wherein at least one of the upper fluid and the lower fluid is thixotropic or shear thickening.

Enumerated Embodiment 51. The formulation of any one of the enumerated embodiments, wherein the volume ratio of the upper fluid and the lower fluid is about 20:1, about 10:1, about 9:1, about 8:1, about 7:1, about 6:1, about 5:1, about 4:1, about 3:1, about 2:1, 1.9:1, about 1.8:1, about 1.7:1, about 1.6:1, about 1.5:1, about 1.4:1, about 1.3:1, about 1.2:1, about 1.1:1, about 1:1, about 1:1.1, about 1:1.2. about 1:1.3, about 1:1.4, about 1:1.5, about 1:1.6, about 1:1.7, about 1:1.8, about 1:1.9, about 1:2, about 1:3, about 1:4, about 1:5, about 1:6, about 1:7, about 1:8, about 1:9, about 1:10, or about 1:20.

Enumerated Embodiment 52. The formulation of any one of the enumerated embodiments, wherein the lower fluid is at least about 1%, at least about 2%, at least about 3%, at least about 4%, at least about 5%, at least about 6%, at least about 7%, at least about 8%, at least about 9%, at least about 10%, at least about 12%, at least about 14%, at least about 16%, at least about 18%, at least about 20%, at least about 22%, at least about 24%, at least about 26%, at least about 28%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% more dense than the upper fluid.

Enumerated Embodiment 53. The formulation of any one of the enumerated embodiments, wherein at least one of the upper fluid and the lower fluid has a viscosity of less than about 0.5, less than about 0.6, less than about 0.7, less than about 0.8, less than about 0.9, less than about 1, less than about 10, less than about 25, less than about 50, less than about 75, less than about 100, less than about 250, less than about 500, less than about 750, less than about 1000, less than about 1250, less than about 1500, less than about 1750, less than about 2000, less than about 2250, less than about 2500, less than about 2750, or less than about 3000 centipoise (cP).

Enumerated Embodiment 54. The formulation of any one of the enumerated embodiments, wherein at least one of the upper fluid and the lower fluid has a viscosity of at least about 0.5, at least about 0.6, at least about 0.7, at least about 0.8, at least about 0.9, at least about 1, at least about 10, at least about 25, at least about 50, at least about 75, at least about 100, at least about 250, at least about 500, at least about 750, at least about 1000, at least about 1250, at least about 1500, at least about 1750, at least about 2000, at least about 2250, at least about 2500, at least about 2750, or at least about 3000 centipoise (cP).

Enumerated Embodiment 55. A device for delivery of a formulation to an olfactory region of a nasal cavity, the device comprising:

a. one or more fluid reservoirs configured to contain a formulation configured to form:
   i. an upper fluid; and
   ii. a lower fluid, immiscible with the upper fluid at intranasal environmental conditions and having a greater density than that of the upper fluid;

wherein at intranasal environmental conditions, one or more volumes of the formulation each form an upper layer comprising the upper fluid and a lower layer comprising the lower fluid;

b. a dispensing tip for delivering the formulation to the olfactory region, wherein the dispensing tip is coupled with the one or more fluid reservoirs; and c. a dispensing mechanism for exerting pressure on the upper fluid and on the lower fluid such that the upper fluid and the lower fluid each flow through the dispensing tip, thereby dispensing the formulation to the olfactory region.

Enumerated Embodiment 56. The device of any one of the enumerated embodiments, wherein the upper fluid comprises a therapeutic agent.

Enumerated Embodiment 57. The device of any one of the enumerated embodiments, wherein the therapeutic agent is preferentially soluble in the upper fluid, and wherein the formulation optionally comprises a second therapeutic agent which is preferentially soluble in the lower fluid.

Enumerated Embodiment 58. The device of any one of the enumerated embodiments, wherein the upper fluid is configured to deliver the therapeutic agent to the nasal cavity and the lower fluid is configured to increase a residence time of the therapeutic agent within the nasal cavity.

Enumerated Embodiment 59. The device of any one of the enumerated embodiments, wherein the upper fluid is configured to deliver the therapeutic agent to an olfactory cleft of the nasal cavity and the lower fluid is configured to at least partially obstruct a lower aspect of the olfactory cleft.

Enumerated Embodiment 60. The device of any one of the enumerated embodiments, wherein the olfactory region comprises an olfactory cleft.

Enumerated Embodiment 61. The device of any one of the enumerated embodiments, wherein the dispensing mechanism is configured to dispense the upper fluid and the lower fluid sequentially.

Enumerated Embodiment 62. The device of any one of the enumerated embodiments, wherein the dispensing mechanism is configured to dispense the upper fluid first, to deliver a therapeutic agent to the nasal cavity, and the lower fluid is second, to purge a residual amount of the upper fluid from the device.

Enumerated Embodiment 63. The device of any one of the enumerated embodiments, wherein the dispensing mechanism is configured to dispense the upper fluid and the lower fluid simultaneously.

Enumerated Embodiment 64. The device of any one of the enumerated embodiments, comprising a single fluid reservoir for storage of the upper fluid and the lower fluid.

Enumerated Embodiment 65. The device of any one of the enumerated embodiments, wherein the fluid reservoir is configured to be pressurized such that the upper fluid and the lower fluid are stored as a homogenous mixture which separates after delivery of the homogenous mixture.

Enumerated Embodiment 66. The device of any one of the enumerated embodiments, wherein the fluid reservoir is configured to store the upper fluid and the lower fluid as stacked layers.

Enumerated Embodiment 67. The device of any one of the enumerated embodiments, additionally comprising a viewing window to allow for evaluation of the mixing or layering of the two fluids within the single fluid reservoir.

Enumerated Embodiment 68. The device of any one of the enumerated embodiments, wherein the single fluid reservoir has an exit port positioned such that when the device is held in a specified orientation during dispensing, the upper fluid is dispensed before the lower fluid.

Enumerated Embodiment 69. The device of any one of the enumerated embodiments, wherein the exit port is positioned away from a central axis running vertically through the fluid reservoir when the device is in an upright orientation.

Enumerated Embodiment 70. The device of any one of the enumerated embodiments, comprising separate fluid reservoirs for separate storage of the upper fluid and the lower fluid.

Enumerated Embodiment 71. The device of any one of the enumerated embodiments, additionally comprising a blending mechanism for mixing the upper fluid and the lower fluid prior to dispensing.

Enumerated Embodiment 72. The device of any one of the enumerated embodiments, additionally comprising a damping mechanism configured to control dispensing of the two fluids.

Enumerated Embodiment 73. The device of any one of the enumerated embodiments, wherein the damping mechanism is a position dependent damping mechanism.

Enumerated Embodiment 74. The device of any one of the enumerated embodiments, wherein the damping mechanism is a two-stage position dependent damping mechanism, wherein the first stage is more strongly damped than the second stage or wherein the second stage is more strongly damped than the first stage.

Enumerated Embodiment 75. The device of any one of the enumerated embodiments, wherein the damping mechanism is configured to provide first stage damping during dispensing of the upper fluid and second stage damping during dispensing of the lower fluid.

Enumerated Embodiment 76. The device of any one of the enumerated embodiments, wherein the damping mechanism is configured to limit shear forces to the upper fluid during ejection, so as to minimize damage to the therapeutic agent.

Enumerated Embodiment 77. The device of any one of the enumerated embodiments, wherein the damping mechanism is an internal damping mechanism configured to use the lower fluid as a damping fluid.

Enumerated Embodiment 78. The device of any one of the enumerated embodiments, wherein the damping mechanism is an external damping mechanism configured to use a separate damping fluid in an external dashpot chamber.

Enumerated Embodiment 79. The device of any one of the enumerated embodiments, wherein the separate damping fluid has a viscosity of at least about 1, at least about 10, at least about 25, at least about 50, at least about 75, at least about 100, at least about 250, at least about 500, at least about 750, at least about 1000, at least about 1250, at least about 1500, at least about 1750, at least about 2000, at least about 2250, at least about 2500, at least about 2750, or at least about 3000 centipoise (cP).

Enumerated Embodiment 80. The device of any one of the enumerated embodiments, wherein the damping mechanism comprises a piston within a cylinder, wherein the cylinder has a change in diameter at a position along the length of the cylinder.

Enumerated Embodiment 81. The device of any one of the enumerated embodiments, wherein the damping mechanism comprises a piston within a cylinder, wherein the piston comprises a piston head having one or more holes for one or more rods to pass through, and wherein the one or more rods have variable diameters.

Enumerated Embodiment 82. The device of any one of the enumerated embodiments, wherein the one or more rods have one or more diameter changes along their length.

Enumerated Embodiment 83. The device of any one of the enumerated embodiments, wherein the damping mechanism comprises a fixed orifice plate within one of the fluid reservoirs and one or more rods configured to pass through one or more holes in the orifice plate.

Enumerated Embodiment 84. The device of any one of the enumerated embodiments, wherein the damping mechanism comprises a fixed orifice plate within one of the fluid reservoirs and one or more dumbbell-shaped pins configured to pass through one or more holes in the orifice plate.

Enumerated Embodiment 85. The device of any one of the enumerated embodiments, wherein the damping mechanism comprises a movable orifice plate within one of the fluid reservoirs and one or more rods configured to pass through one or more holes in the orifice plate.

Enumerated Embodiment 86. The device of any one of the enumerated embodiments, additionally comprising a lock-out mechanism configured to prevent dispensing if the device is in an undesirable orientation.

Enumerated Embodiment 87. The device of any one of the enumerated embodiments, wherein the one or more fluid reservoirs further comprises a coupling member, the coupling member configure to be couplable with the dispensing tip.

Enumerated Embodiment 88. The device of any one of the enumerated embodiments, wherein the coupling member is configured to be movable within the one or more fluid reservoirs along a central axis running vertically through the one or more fluid reservoirs.

Enumerated Embodiment 89. The device of any one of the enumerated embodiments, wherein the dispensing member is configured to exert pressure on the movable coupling member, thereby causing the upper fluid to flow through the dispensing tip.

Enumerated Embodiment 90. The device of any one of the enumerated embodiments, wherein the coupling member comprises a self-healing rubber.

Enumerated Embodiment 91. The device of any one of the enumerated embodiments, wherein the upper fluid and the lower fluid are separated by a separating member in the one or more fluid reservoirs.

Enumerated Embodiment 92. The device of any one of the enumerated embodiments, wherein the separating member is configured to be movable within the one or more fluid reservoirs along a central axis running vertically through the one or more fluid reservoirs.

Enumerated Embodiment 93. The device of any one of the enumerated embodiments, wherein the separating member comprises a pre-punctured hole.

Enumerated Embodiment 94. The method of any one of the enumerated embodiments, wherein the upper fluid is delivered through a dispensing tip and the lower fluid purges a residual amount of the upper fluid from the device, thereby reducing a tail-off phase.

Enumerated Embodiment 95. The method of any one of the enumerated embodiments, wherein the upper fluid is delivered through a dispensing tip and the lower fluid purges a residual amount of the upper fluid from the device, thereby reducing wasted upper fluid.

Enumerated Embodiment 96. The method of any one of the enumerated embodiments, wherein the upper fluid is delivered through a dispensing tip and the presence of the ejected lower fluid minimizes the disruption to the tail of the upper fluid and preserves its cohesion.

All publications, patents, and patent applications mentioned in this specification are herein incorporated by reference to the same extent as if each individual publication, patent, or patent application was specifically and individually indicated to be incorporated by reference.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and devices within the scope of these claims and their equivalents be covered thereby.

What is claimed is:

1. A method of concentrating an upper fluid against an olfactory region of a nasal cavity of a subject, the method comprising:

a. delivering a formulation to the olfactory region of the nasal cavity, the formulation configured to form:

i. the upper fluid; and ii. a lower fluid, immiscible with the upper fluid at intranasal environmental conditions and having a greater density than that of the upper fluid, such that the upper fluid amasses on top of the lower fluid;

wherein the upper fluid and the lower fluid are delivered simultaneously, wherein the formulation delivered to the olfactory region of the nasal cavity forms an upper layer comprising the upper fluid and a separate lower layer comprising the lower fluid, the upper layer impacting the olfactory region and the separate lower layer supporting the upper layer, thereby concentrating the upper fluid against the olfactory region of the nasal cavity.

2. The method of claim 1, wherein the olfactory region comprises an olfactory cleft of the nasal cavity.

3. The method of claim 1, wherein the upper fluid comprises a therapeutic agent.

4. The method of claim 3, wherein the therapeutic agent is preferentially soluble in the upper fluid.

5. The method of claim 3, wherein the upper fluid delivers the therapeutic agent to the olfactory region of the nasal cavity, and the lower fluid increases a residence time of the therapeutic agent within the nasal cavity.

6. The method of claim 3, wherein the upper fluid delivers the therapeutic agent to an olfactory cleft of the olfactory region of the nasal cavity, and the lower fluid at least partially obstructs a lower aspect of the olfactory cleft of the olfactory region of the nasal cavity.

7. The method of claim 1, wherein the lower fluid comprises a therapeutic agent.

8. The method of claim 1, wherein the upper fluid comprises a first therapeutic agent, preferentially soluble in the upper fluid, and the lower fluid comprises a second therapeutic agent, preferentially soluble in the lower fluid.

9. The method of claim 8, wherein the first therapeutic agent is delivered to the olfactory region of the subject, and the second therapeutic agent affects a tissue so as to influence absorption of the first therapeutic agent.

10. The method of claim 8, wherein the first therapeutic agent is delivered to the olfactory region of the subject, and the second therapeutic agent improves delivery of the first therapeutic agent to the olfactory region.

11. The method of claim 1, wherein the upper fluid comprises a sampling fluid which collects a biological material from the olfactory region of the nasal cavity.

12. The method of claim 11, wherein the olfactory region of the nasal cavity is an olfactory cleft.

13. The method of claim 11, additionally comprising analyzing the sampling fluid to evaluate the collected biological material.

14. The method of claim 1, wherein the lower fluid forms a capillary bridge at a lower aspect of an olfactory cleft of the olfactory region of the nasal cavity.

15. The method of claim 14, wherein the capillary bridge contacts opposing sides of the olfactory region of the subject's nasal cavity, and supports a coating of the formulation about the olfactory cleft.

16. The method of claim 1, wherein the olfactory region of the nasal cavity comprises an underside of a cribriform plate of the nasal cavity.

17. The method of claim 1, wherein the formulation is delivered as a homogenous formulation which separates after the delivery.

18. A method of delivering a therapeutic agent to an olfactory region of a nasal cavity of a subject, the method comprising:

a. delivering a formulation to the olfactory region of the nasal cavity, the formulation configured to form:

i. an upper fluid comprising the therapeutic agent; and ii. a lower fluid, immiscible with the upper fluid at intranasal environmental conditions and having a greater density than that of the upper fluid, such that the upper fluid amasses on top of the lower fluid;

wherein the upper fluid and the lower fluid are delivered simultaneously, wherein the formulation delivered to the olfactory region of the nasal cavity forms an upper layer comprising the upper fluid and a separate lower layer comprising the lower fluid, the upper layer impacting the olfactory region and the separate lower layer supporting the upper layer, thereby concentrating the upper fluid against the olfactory region of the nasal cavity and delivering the therapeutic agent to the olfactory region of the nasal cavity.

* * * * *